United States Patent [19]
Barbacid et al.

[11] Patent Number: 5,348,856
[45] Date of Patent: Sep. 20, 1994

[54] DNA ENCODING TRKC PROTEIN

[75] Inventors: Mariano Barbacid, Lawrenceville; Fabienne Lamballe, Plainsboro, both of N.J.

[73] Assignee: E. R. Squibb & Sons, Inc., Princeton, N.J.

[21] Appl. No.: 912,952

[22] Filed: Jul. 7, 1992

Related U.S. Application Data

[63] Continuation-in-part of Ser. No. 726,466, Jul. 8, 1991, abandoned.

[51] Int. Cl.$^5$ .................. C07K 13/00; C12N 15/12; C12N 15/63
[52] U.S. Cl. ......................... 435/6; 435/69.1; 435/252.3; 435/320.1; 530/350; 536/23.5
[58] Field of Search ................. 435/69.1, 6, 252.3, 435/320.1; 530/350; 536/27, 23.5

[56] References Cited

PUBLICATIONS

EMBO J. 8:3701–3709, 1989, Klein et al. trkB, a novel tyrosine protein kinase receptor expressed during mouse neural development.
F. Lamballe et al., Cell, vol. 66, No. 5, pp. 967–979, 1991.
F. Lamballe et al., Journal of Cellular Biochemistry, Supplement O, vol. 15, No. B, p. 212, paragraph 2, 1991.
S. K. Hanks et al., Science, 241, pp. 42–52, 1988.
B. L. Hempsted et al., Nature, 350, pp. 678–683, 1991.
D. R. Kaplan et al., Science, 252, pp. 554–557, 1991.
D. R. Kaplan et al., Nature, 350, pp. 158–160, 1991.
R. Klein et al., Cell, 61, pp. 647–656, 1990.
R. Klein et al., Development, 109, pp. 845–850, 1990.
R. Klein et al., Cell, 65, pp. 189–197, 1991.
C. Lai et al., Neuron, 6, pp. 691–704, 1991.
D. Middlemas et al., Mol. Cell. Biol., 11, pp. 143–153, 1991.
A. R. Nebreda et al., Science, 252, pp. 558–561, 1991.
D. Soppet et al., Cell, 65, pp. 895–903, 1991.
S. P. Squinto et al., Cell, 65, pp. 885–893, 1991.
A. Ullrich et al., Cell, 61, pp. 203–212, 1990.
G. Mitra, Proc. Natl. Acad. Sci. USA, 84, pp. 6707–6711, 1987.
S. Kozma, EMBO J., 7, pp. 147–154, 1988.
F. Coulier et al., Mol. Cell. Biol., 9, pp. 15–24, 1989.
D. Martin-Zanca et al., Nature, 319, pp. 743–748, 1986.
D. Martin-Zanca et al., Mol. Cell. Bol. 9, pp. 24–33, 1989.
R. Oskam et al., Proc. Natl. Acad. Sci. USA, 85, pp. 2964–2968, 1988.

*Primary Examiner*—Robert J. Hill, Jr.
*Assistant Examiner*—John D. Ulm
*Attorney, Agent, or Firm*—Timothy J. Gaul

[57] ABSTRACT

Nucleic acid sequences, particularly DNA sequences, coding for all or part of a trkC protein, expression vectors containing the DNA sequences, host cells containing the expression vectors, and methods utilizing these materials. The invention also concerns polypeptide molecules comprising all or part of a trkC protein and methods for producing these polypeptide molecules.

18 Claims, 7 Drawing Sheets

FIG. 1B

```
   1 CGGGCTCCGATAACCGAAGCAGCGATCGGAGATGGATGTCTCTCTTTGCCCAGCCAAGTG   60
                                   M  D  V  S  L  C  P  A  K  C   10

61 TAGTTTCTGGCGGATTTTCTTGCTGGGAAGCGTCTGGCTGGACTATGTGGGCTCCGTGCT  120
      S  F  W  R  I  F  L  L  G  S  V  W  L  D  Y  V  G  S  V  L   30

121 GGCTTGCCCTGCAAATTGTGTCTGCAGCAAGACTGAGATCAATTGCCGGCGGCCGGACGA  180
      A  C  P  A  N  C  V  C  S  K  T  E  I  N  C  R  R  P  D  D   50

181 TGGGAACCTCTTCCCCCTCCTGGAAGGGCAGGATTCAGGGAACAGCAATGGGAATGCCAG  240
      G  N  L  F  P  L  L  E  G  Q  D  S  G  N  S  N  G  N  A  S   70

241 CATCAACATCACGGACATCTCAAGGAATATCACTTCCATACACATAGAGAACTGGCGCGG  300
      I  N  I  T  D  I  S  R  N  I  T  S  I  H  I  E  N  W  R  G   90

301 TCTGCACACGCTCAACGCTGTGGACATGGAGCTCTACACCGGCCTCCAGAAGCTGACCAT  360
      L  H  T  L  N  A  V  D  M  E  L  Y  T  G  L  Q  K  L  T  I  110

361 CAAGAACTCAGGACTTCGGAGCATCCAGCCCAGAGCCTTTGCCAAGAACCCCCACCTGCG  420
      K  N  S  G  L  R  S  I  Q  P  R  A  F  A  K  N  P  H  L  R  130

421 CTACATAAACCTGTCGAGTAACCGGCTCACCACACTCTCATGGCAGCTCTTCCAGACGCT  480
      Y  I  N  L  S  S  N  R  L  T  T  L  S  W  Q  L  F  Q  T  L  150

481 GAGTCTTCGGGAATTGAGATTGGAGCAGAACTTCTTCAACTGCAGCTGTGACATCCGCTG  540
      S  L  R  E  L  R  L  E  Q  N  F  F  N  C  S  C  D  I  R  W  170

541 GATGCAGCTGTGGCAGGAGCAGGGGGAGGCCAAGCTGAACAGCCAGAGCCTCTATTGCAT  600
      M  Q  L  W  Q  E  Q  G  E  A  K  L  N  S  Q  S  L  Y  C  I  190

601 CAGTGCCGATGGCTCCCAGCTCCCCCTCTTCCGCATGAACATTAGCCAGTGTGACCTTCC  660
      S  A  D  G  S  Q  L  P  L  F  R  M  N  I  S  Q  C  D  L  P  210

661 TGAGATCAGTGTGAGCCACGTCAATCTGACCGTTCGGGAGGGTGACAATGCTGTTGTCAC  720
      E  I  S  V  S  H  V  N  L  T  V  R  E  G  D  N  A  V  V  T  230

721 CTGCAATGGCTCTGGATCACCCCTGCCCGACGTGGACTGGATCGTCACTGGACTGCAGTC  780
      C  N  G  S  G  S  P  L  P  D  V  D  W  I  V  T  G  L  Q  S  250

781 CATCAACACCCACCAGACAAATCTGAATTGGACCAACGTACACGCCATCAACCTGACACT  840
      I  N  T  H  Q  T  N  L  N  W  T  N  V  H  A  I  N  L  T  L  270

841 GGTCAATGTGACGAGTGAGGACAACGGCTTCACCCTGACGTGCATTGCAGAGAACGTGGT  900
      V  N  V  T  S  E  D  N  G  F  T  L  T  C  I  A  E  N  V  V  290

901 GGGCATGAGCAATGCCAGCGTCGCCCTCACTGTTCACTACCCCCCACGAGTGGTGAGCCT  960
      G  M  S  N  A  S  V  A  L  T  V  H  Y  P  P  R  V  V  S  L  310

961 GGAGGAGCCAGAGCTGCGCCTGGAACACTGCATCGAGTTTGTGGTGCGTGGCAACCCGCC 1020
      E  E  P  E  L  R  L  E  H  C  I  E  F  V  V  R  G  N  P  P  330

1021 GCCCACGCTGCACTGGCTGCACAACGGGCAGCCGCTGCGTGAGTCCAAGATCACCCACGT 1080
      P  T  L  H  W  L  H  N  G  Q  P  L  R  E  S  K  I  T  H  V  350

1081 GGAGTACTACCAGGAGGGCGAGGTCTCCGAGGGCTGCCTGCTCTTCAACAAGCCCACCCA 1140
      E  Y  Y  Q  E  G  E  V  S  E  G  C  L  L  F  N  K  P  T  H  370

1141 CTACAACAATGGCAACTACACACTCAATCGCCAAGAACCCCTTGGCACAGCCAACCAGAC 1200
      Y  N  N  G  N  Y  T  L  N  R  Q  E  P  L  G  T  A  N  Q  T  390

1201 CATCAATGGCCACTTCCTCAAGGAGCCTTTTCCAGAGAGCACGGATAACTTTGTCTCTTT 1260
      I  N  G  H  F  L  K  E  P  F  P  E  S  T  D  N  F  V  S  F  410

1261 CTATGAAGTGAGCCCCACCCCTCCCATCACTGTGACGCACAAGCCAGAGGAAGATACATT 1320
      Y  E  V  S  P  T  P  P  I  T  V  T  H  K  P  E  E  D  T  F  430
```

```
1321 TGGGGTATCCATAGCTGTTGGACTTGCCGCTTTTGCCTGTGTCCTTCTGGTGGTTCTCTT 1380
      G  V  S  I  A  V  G  L  A  A  F  A  C  V  L  L  V  V  L  F   450
1381 TATCATGATCAACAAGTATGGTCGACGGTCTAAATTTGGAATGAAGGGTCCTGTGGCTGT 1440
      I  M  I  N  K  Y  G  R  R  S  K  F  G  M  K  G  P  V  A  V   470
1441 CATCAGTGGTGAAGAGGACTCAGCCAGCCCACTGCATCACGATCAACCATGGCATCACCA 1500
      I  S  G  E  E  D  S  A  S  P  L  H  H  D  Q  P  W  H  H  H   490
1501 CACCCTCATCACTGGACGCCGGGCCGGACACAGTGTCATTGGCATGACCCGCATCCCAGT 1560
      T  L  I  T  G  R  R  A  G  H  S  V  I  G  M  T  R  I  P  V   510
1561 CATTGAGAACCCCCAGTACTTCCGCCAGGGACACAACTGCCACAAGCCAGACACGTATGT 1620
      I  E  N  P  Q  Y  F  R  Q  G  H  N  C  H  K  P  D  T  Y  V   530
1621 GCAGCACATTAAAAGGAGGGACATCGTGCTGAAGCGAGAACTGGGTGAGGAGCCTTTGG 1680
      Q  H  I  K  R  R  D  I  V  L  K  R  E  L  G  E  G  A  F  G   550
                                              TK
1681 GAAGGTCTTCCTGGCCGAGTGCTACAACCTCAGCCCCACCAAGGTCAAGATGCTCGTGGC 1740
      K  V  F  L  A  E  C  Y  N  L  S  P  T  K  V  K  M  L  V  A   570
1741 TGTGAAGGCCCTGAAGGATCCCACCCTGGCCGCCCGGAAGGATTTCCAGAGGGAGGCTGA 1800
      V  K  A  L  K  D  P  T  L  A  A  R  K  D  F  Q  R  E  A  E   
1801 GCTGCTCACCAACCTGCAGCATGAGCACATTGTCAAGTTCTATGGGGTGTGCGGCGACGG 1860
      L  L  T  N  L  Q  H  E  H  I  V  K  F  Y  G  V  C  G  D  G   610
1861 GGACCCACTCATCATGGTTTTTGAGTACATGAAACACGGGGATCTGAACAAGTTCCTCAG 1920
      D  P  L  I  M  V  F  E  Y  M  K  H  G  D  L  N  K  F  L  R   630
1921 GGCCCATGGGCCAGATGCCATGATCCTCGTGGACGGCCAGCCACGCCAGGCAAAAGGCGA 1980
      A  H  G  P  D  A  M  I  L  V  D  G  Q  P  R  Q  A  K  G  E   650
1981 GCTGGGGCTCTCCCAGATGCTGCACATTGCCAGTCAGATCTGCTCTGGCATGGTGTACCT 2040
      L  G  L  S  Q  M  L  H  I  A  S  Q  I  C  S  G  M  V  Y  L   670
2041 GGCCTCCCAGCATTTTGTGCACCGGGACCTGGCCACCAGGAACTGCCTGGTTGGAGCCAA 2100
      A  S  Q  H  F  V  H  R  D  L  A  T  R  N  C  L  V  G  A  N   690
2101 CCTGCTGGTGAAGATTGGCGATTTCGGCATGTCCAGAGATGTCTACAGCACGGATTACTA 2160
      L  L  V  K  I  G  D  F  G  M  S  R  D  V  Y  S  T  D  Y  Y   710
2161 CAGGGTAGGAGGACACACCATGCTCCCAATTCGCTGGATGCCTCCTGAAAGCATCATGTA 2220
      R  V  G  G  H  T  M  L  P  I  R  W  M  P  P  E  S  I  M  Y   730
2221 CCGGAAGTTCACTACTGAGAGTGACGTGTGGAGCTTCGGGGTGATCCTCTGGGAGATCTT 2280
      R  K  F  T  T  E  S  D  V  W  S  F  G  V  I  L  W  E  I  F   750
2281 CACCTACGGAAAGCAGCCATGGTTCCAACTCTCAAACACAGAGGTCATTGAGTGCATCAC 2340
      T  Y  G  K  Q  P  W  F  Q  L  S  N  T  E  V  I  E  C  I  T   770
2341 CCAAGGTCGCGTTTTGGAACGGCCCCGGGTCTGCCCCAAAGAGGTGTATGATGTCATGCT 2400
      Q  G  R  V  L  E  R  P  R  V  C  P  K  E  V  Y  D  V  M  L   790
2401 GGGGTGCTGGCAGAGGGAACCGCAGCAGCGGCTGAACATCAAGGAAATCTACAAAATCCT 2460
      G  C  W  Q  R  E  P  Q  Q  R  L  N  I  K  E  I  Y  K  I  L   810
                                                              TK
2461 CCATGCTTTGGGGAAAGCCACCCCCATCTACCTGGACATCCTTGGCTAGCGGTGGCCGGT 2520
      H  A  L  G  K  A  T  P  I  Y  L  D  I  L  G  ...              825
2521 GGTCAC 2526
```

FIG. 1C

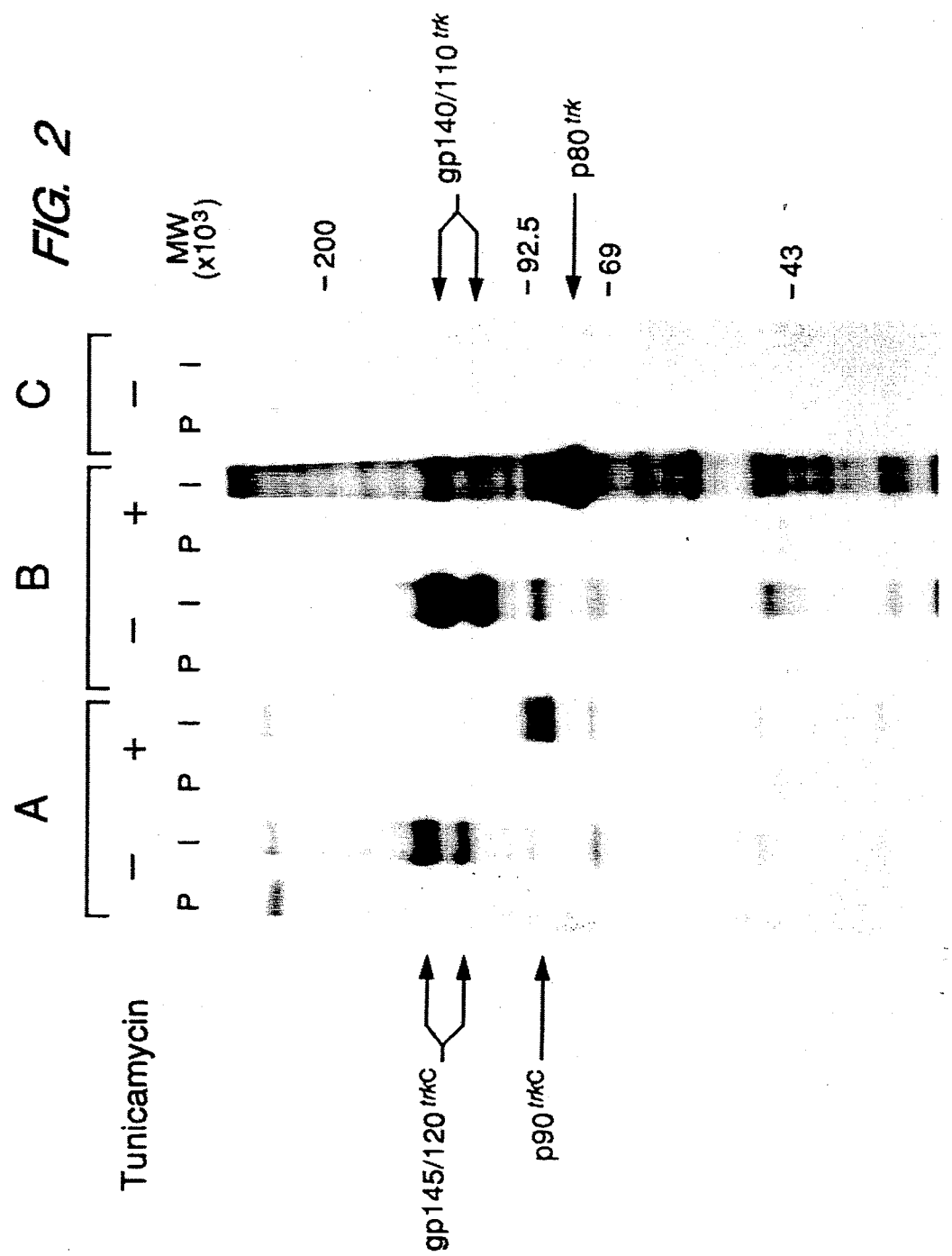

*trk* C external domain

ß-actin

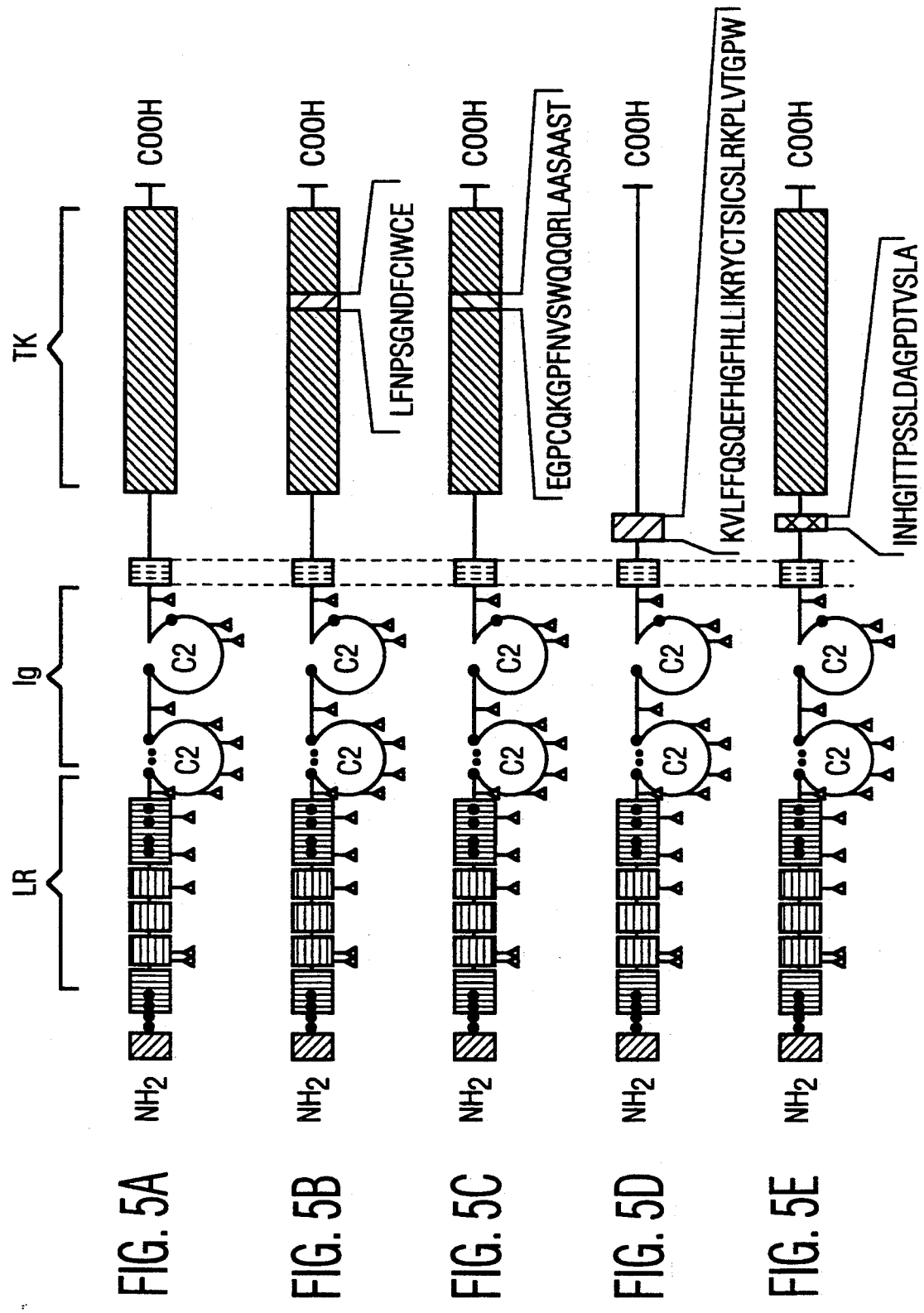

DNA ENCODING TRKC PROTEIN

This application is a continuation-in-part of U.S. Ser. No. 07/726,466 filed on Jul. 8, 1991, abandoned.

BACKGROUND OF THE INVENTION

The existence of oncogenes has been known for some time. An oncogene may be broadly defined as a gene whose protein product, when present in certain host cells, can transform the cells to a cancerous phenotype. A proto-oncogene, on the other hand, may be broadly defined as a normal gene which can become "activated" to yield an oncogene. The first oncogenes discovered were the transforming genes of certain oncogenic viruses. Subsequently, it was discovered that oncogenes are also present in various eucaryotic cells. Included among these oncogenes is the oncogene designated as trk.

The trk locus was first identified in a human colon carcinoma where it became activated as an oncogene by a chromosomal rearrangement which fused its transmembrane and catalytic domains to a subset of sequences derived from a non-muscle tropomyosin gene. Martin-Zanca, D. et al., Nature 319, 743-748 (1986). Additional trk oncogenes carrying activating sequences other than tropomyosin have been generated during the course of gene transfer assays. Kozma et al., EMBO J. 9, 147-154 (1988); Oskam et al., Proc. Natl. Acad. Sci. 9, 2964-2968 (1988). The trk proto-oncogene codes for a cell surface receptor with tyrosine protein kinase activity that is specifically expressed in the trigeminal and certain dorsal root ganglia.

A gene related to the trk proto-oncogene and designated trkB has recently been isolated from a mouse brain cDNA library. Klein, R. et al., EMBO J. 8, 3701-3709 (1989). The trkB proto-oncogene also codes for a cell surface receptor with tyrosine protein kinase activity. Mutated alleles (oncogenes) of both of these genes can trigger malignant transformation.

The present invention involves the discovery of a third gene related to the trk proto-oncogene, trkC.

SUMMARY OF THE INVENTION

The present invention concerns an isolated nucleic acid molecule comprising a nucleic acid sequence coding for all or part of a trkC protein. Preferably, the nucleic acid molecule is a DNA (deoxyribonucleic acid) molecule, and the nucleic acid sequence is a DNA sequence. Further preferred is a DNA sequence having all or part of the nucleotide sequence substantially as shown in FIG. 1B (SEQ. ID NO: 1).

The present invention further concerns expression vectors comprising a DNA sequence coding for all or part of a trkC protein.

The present invention additionally concerns prokaryotic or eukaryotic host cells containing an expression vector which comprises a DNA sequence coding for all or part of a trkC protein.

The present invention also concerns methods for detecting nucleic acid sequences coding for all or part of a trkC protein (SEQ. ID. NO. 2) or related nucleic acid sequences.

The present invention further concerns polypeptide molecules comprising all or part of a trkC protein.

DESCRIPTION OF THE FIGURES

FIGS. 1A to 1C. Nucleotide sequence analysis of the 2526 bp long insert of pFL19, a cDNA clone of the porcine trkC gene. (A) Schematic representation of pFL19. The thick bar represent coding sequences flanked by the initiating (ATG) and terminating (TAG) codons. The putative signal peptide (SP, dotted box), transmembrane (TM, black box) and tyrosine kinase (TK, hatched box) domains are indicated. Other symbols represent cysteine residues (closed dots) and consensus N-glycosylation sites (inverted triangles) present in the extracellular domain. Thin open bars represent 5' and 3' non-coding sequences. (B and C) Nucleotide and deduced amino acid sequence of the 2526 bp insert of pFL19. The putative signal peptide (amino acids 1-31) is highlighted by a dotted box. The unique Nae I site used to fuse the pFL7 and pFL15 cDNA clones into pFL19 (see text) is overlined. The consensus N-glycosylation sites are underlined by open bars. The cysteine residues in the extracellular domain are circled. The putative transmembrane domain (amino acid residues 430-453) is underlined by a solid bar. The tyrosine kinase catalytic domain (amino acids 544-810) is flanked by horizontal arrows. The in-frame frame terminator codon TAG (positions 2507 to 2509) is indicated by asterisks.

FIG. 2. Identification of the trkC products. [$^{35}$S]methionine-labeled cell extracts of (A) NIH3T3 cells transfected with the expression plasmid pFL20, (B) NIH3T3 cells expressing the trk proto-oncogene products and (C) parental NIH3T3 cells were grown either in absence (−) or presence (+) of 10 μg/ml of tunicamycin and submitted to immunoprecipitation analysis with preimmune (P) or immune (I) serum raised against a peptide corresponding to the 14 carboxy-terminal amino acids of the trk proto-oncogene product. The migration of the glycosylated gp145/120$^{trkC}$ and gp140/110$^{trkC}$ molecules and their corresponding polypeptidic backbones p90$^{trkC}$ and p80$^{trkC}$ are indicated by arrows. Co-electrophoresed molecular weight markers include myosin (200,00), phosphorylase B (92,500), bovine serum albumin (69,000) and ovalbumin (43,000).

FIGS. 5 and 5E. Schematic representation of (A) TrkC K1, (B) TrkC K2, (C) TrkC K3, (D) TrkC NC2 and (E) TrkC NC1.

DETAILED DESCRIPTION OF THE INVENTION

Figure 1A:
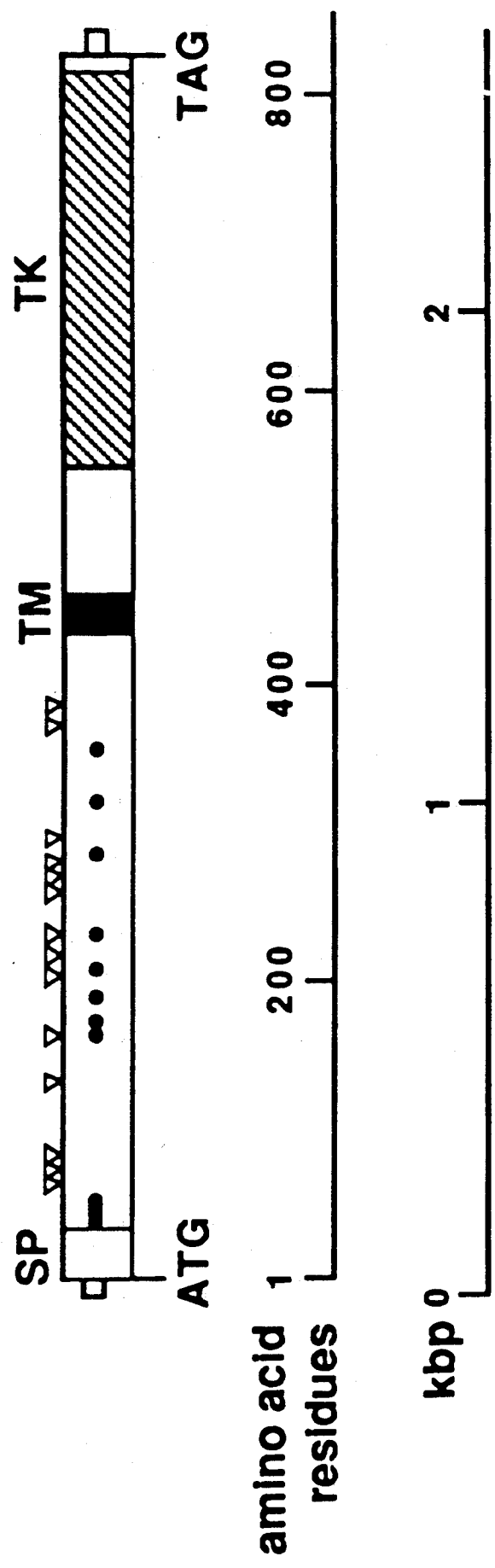

The present invention concerns an isolated nucleic acid molecule comprising a nucleic acid sequence coding for all or part of a trkC protein. Preferably, the nucleic acid molecule is a DNA molecule and the nucleic acid sequence is a DNA sequence. Further preferred is a DNA sequence having all or part of the nucleotide sequence substantially as shown in FIG. 1B (SEQ. ID NO: 1), or a DNA sequence complementary to this DNA sequence. In the case of a nucleotide sequence (e.g., a DNA sequence) coding for part of a trkC protein, it is preferred that the nucleotide sequence be at least about 15 nucleotides in length.

The DNA sequences of the present invention can be isolated from a variety of sources, although the presently preferred sequences have been isolated from porcine and murine cDNA libraries. The exact amino acid sequence of the polypeptide molecule produced will vary with the initial DNA sequence.

The DNA sequences of the present invention can be obtained using various methods well-known to those of ordinary skill in the art. At least three alternative principal methods may be employed:

(1) the isolation of a double-stranded DNA sequence from genomic DNA or complementary DNA (cDNA) which contains the sequence;
(2) the chemical synthesis of the DNA sequence; and
(3) the synthesis of the DNA sequence by polymerase chain reaction (PCR).

In the first approach, a genomic or cDNA library can be screened in order to identify a DNA sequence coding for all or part of a trkC protein. For example, a porcine or murine cDNA library can be screened in order to identify a DNA sequence coding for all or part of a trkC protein. Various porcine and murine cDNA libraries, for example brain cDNA libraries, can be employed. Various techniques can be used to screen the genomic DNA or cDNA libraries.

For example, labeled single stranded DNA probe sequences duplicating a sequence present in the target genomic DNA or cDNA coding for all or part of a trkC protein can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of a trkC protein using immunoblotting techniques.

In one typical screening method suitable for either immunoblotting or hybridization techniques, the genomic DNA library, which is usually contained in a vector such as λGT11, or cDNA library is first spread out on agarose plates, and then the clones are transferred to filter membranes, for example, nitrocellulose membranes. A DNA probe can then be hybridized or an antibody can then be bound to the clones to identify those clones containing the genomic DNA or cDNA coding for all or part of a trkC protein.

In the second approach, the DNA sequence of the present invention coding for all or part of a trkC protein can be chemically synthesized. For example, the DNA sequence coding for a trkC protein can be synthesized as a series of 100 base oligonucleotides that can then be sequentially ligated (via appropriate terminal restriction sites) so as to form the correct linear sequence of nucleotides.

In the third approach, the DNA sequences of the present invention coding for all or part of a trkC protein can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, U.S. Pat. Nos. 4,683,195 and 4,683,202.

The DNA sequences of the present invention can be used in a variety of ways in accordance with the present invention. For example, they can be used as DNA probes to screen other cDNA and genomic DNA libraries so as to select by hybridization other DNA sequences that code for proteins related to a trkC protein. In addition, the DNA sequences of the present invention coding for all or part of a trkC protein can be used as DNA probes to screen other cDNA and genomic DNA libraries to select by hybridization DNA sequences that code for trkC protein molecules from organisms other than pigs and mice.

The DNA sequences of the present invention coding for all or part of a trkC protein can also be modified (i.e., mutated) to prepare various mutations. Such mutations may be either degenerate, i.e., the mutation does not change the amino acid sequence encoded by the mutated codon, or non-degenerate, i.e., the mutation changes the amino acid sequence encoded by the mutated codon. These modified DNA sequences may be prepared, for example, by mutating a trkC protein DNA sequence so that the mutation results in the deletion, substitution, insertion, inversion or addition of one or more amino acids in the encoded polypeptide using various methods known in the art. For example, the methods of site-directed mutagenesis described in Taylor, J. W. et al., Nucl. Acids Res. 13, 8749–8764 (1985) and Kunkel, J. A., Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). Both degenerate and non-degenerate mutations may be advantageous in producing or using the polypeptides of the present invention. For example, these mutations may permit higher levels of production, easier purification, or provide additional restriction endonuclease recognition sites. All such modified DNAs (and the encoded polypeptide molecules) are included within the scope of the present invention.

As used in the present application, the term "modified", when referring to a nucleotide or polypeptide sequence, means a nucleotide or polypeptide sequence which differs from the wildtype sequence found in nature.

The present invention further concerns expression vectors comprising a DNA sequence coding for all or part of a trkC protein. The expression vectors preferably contain all or part of the DNA sequence having the nucleotide sequence substantially as shown in FIG. 1B (SEQ. ID NO: 1). Further preferred are expression vectors comprising one or more regulatory DNA sequences operatively linked to the DNA sequence coding for all or part of a trkC protein. As used in this context, the term "operatively linked" means that the regulatory DNA sequences are capable of directing the replication and/or the expression of the DNA sequence coding for all or part of a trkC protein.

Expression vectors of utility in the present invention are often in the form of "plasmids", which refer to circular double stranded DNAs which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front of (i.e., upstream of) the DNA sequence and followed by the DNA sequence coding for all or part of a trkC protein, transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and sequences which provide sites for cleavage by restriction endonucleases. The characteristics of the actual expression vector used must be compatible with the host cell which is to be employed. For example, when cloning in a mammalian cell system, the expression vector should contain promoters isolated from the genome of mammalian cells, (e.g., mouse metallothionein promoter), or from viruses that grow in these cells (e.g., vaccinia virus 7.5K promoter). An expression vector as contemplated by the present invention is at least capable of directing the replication, and preferably the expression of the DNA sequences of the present invention. Suitable origins of replication include, for example, the Ori origin of replication from the ColE1 derivative of pMB1. Suitable promoters include, for example, the long terminal repeats of the Moloney sarcoma virus, the Rous sarcoma virus and the mouse mammary tumor virus, as well as the early regions of Simian virus 40 and the polyoma virus. As selectable markers, the bacterial genes encoding resistance to the antibodies neomycin and G418 (neo), puromycin (pur) or hygromycin (hygro), or mammalian genes encoding thymidine kinase can be employed. All of these materials are known in the art and are commercially available.

Particularly preferred is the expression vector designated pFL19 described herein below, which contains the DNA sequence coding for a trkC protein, or expression vectors with the identifying characteristics of pFL19.

Plasmid DFL19 was deposited with the American Type Culture Collection, Rockville, Md. on Jul. 3, 1991 under the Budapest Treaty and assigned ATCC accession no. 75046. pFL19 contains a cDNA clone of the trkC protein encompassing the entire coding sequence.

Suitable expression vectors containing the desired coding and control sequences may be constructed using standard recombinant DNA techniques known in the art, many of which are described in Maniatis, T. et al., Molecular Cloning: A Laboratory Manual, Cold Spring Harbor Laboratory, Cold Spring Harbor, N.Y. (1982).

The present invention additionally concerns host cells containing an expression vector which comprises a DNA sequence coding for all or part of a trkC protein. The host cells preferably contain an expression vector which comprises all or part of the DNA sequence having the nucleotide sequence substantially as shown in FIG. 1B (SEQ. ID NO: 1). Further preferred are host cells containing an expression vector comprising one or more regulatory DNA sequences capable of directing the replication and/or the expression of and operatively linked to a DNA sequence coding for all or part of a trkC protein. Suitable host cells include both prokaryotic and eukaryotic cells. Suitable prokaryotic host cells include, for example, various strains of *E. coli* such as DH5α, C600 and LL1. Suitable eukaryotic host cells include, for example, mouse NIH3T3 and BALB3T3 cells, rat Rat-2 cells, monkey COS cells, human Hela cells and hamster CHO cells.

Preferred as host cells are mouse NIH3T3 cells.

Expression vectors may be introduced into host cells by various methods known in the art. For example, transfection of host cells with expression vectors can be carried out by the calcium phosphate precipitation method. However, other methods for introducing expression vectors into host cells, for example, electroporation, biolistic fusion, liposomal fusion, nuclear injection and viral or phage infection can also be employed.

Once an expression vector has been introduced into an appropriate host cell, the host cell can be cultured under conditions permitting expression of large amounts of the desired polypeptide, in this case a polypeptide molecule comprising all or part of a trkC protein. Such polypeptides are useful in the study of the characteristics of a trkC protein, for example, its role in oncogenesis. Such polypeptides can also be used to identify potential anti-cancer drugs. For example, a compound which is able to bind to or inhibit the function of the trkC protein may be an effective cancer chemotherapeutic agent.

In addition, as noted in a co-pending U.S. patent application entitled "Methods for Detection of Neuroactive Substances" listing Mariano Barbacid and Rudiger Klein as co-inventors and being filed on even date herewith, the trkC protein can be used to detect agonists and antagonists of neurotropic factors, such as neurotrophin-3 (NT-3). These methods are based on the findings disclosed in this co-pending patent application that trkC protein is the primary receptor for NT-3, that NT-3 induces the phosphorylation of trkC protein, and that trkC protein mediates the mitogenic activity of NT-3. This co-pending U.S. patent application is incorporated herein by reference.

Host cells containing an expression vector which contains a DNA sequence coding for all or part of a trkC protein may be identified by one or more of the following four general approaches: (a) DNA-DNA hybridization; (b) the presence or absence of marker gene functions; (c) assessing the level of transcription as measured by the production of trkC protein mRNA transcripts in the host cell; and (d) detection of the gene product immunologically.

In the first approach, the presence of a DNA sequence coding for all or part of a trkC protein can be detected by DNA-DNA or RNA-DNA hybridization using probes complementary to the DNA sequence.

In the second approach, the recombinant expression vector host system can be identified and selected based upon the presence or absence of certain marker gene function (e.g., thymidine kinase activity, resistance to antibiotics, etc.). A marker gene can be placed in the same plasmid as the DNA sequence coding for all or part of a trkC protein under the regulation of the same or a different promoter used to regulate a trkC protein coding sequence. Expression of the marker gene in response to induction or selection indicates expression of the DNA sequence coding for all or part of a trkC protein.

In the third approach, the production of a trkC protein mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of a trkC protein can be assessed immunologically, for example, by Western blotting.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463-5467 (1977), or the Maxam-Gilbert method as described in proc. Natl. Acad. Sci. USA 74, 560-564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for detecting a nucleic acid sequence coding for all or part of a trkC protein or a related nucleic acid sequence comprising contacting the nucleic acid sequence with a detectable marker which binds specifically to at least a portion of the nucleic acid sequence, and detecting the marker so bound. The presence of bound marker indicates the presence of the nucleic acid sequence. Preferably, the nucleic acid sequence is a DNA sequence having all or part of the nucleotide sequence substantially as shown in FIG. 1B (SEQ. ID NO: 1). Also preferred is a method in which the DNA sequence is a genomic DNA sequence. A DNA sample containing the DNA sequence may be isolated using various methods for DNA isolation which are well-known to those of ordinary skill in the art. For example, a genomic DNA sample may be isolated from tissue by rapidly freezing the tissue from which the DNA is to be isolated, crushing the tissue to produce readily digestible pieces, placing the crushed tissue in a solution of proteinase K and sodium dodecyl sulfate, and incubating the resulting solution until most of the cellular protein is degraded. The digest is then deprotenized by successive phenol/chloroform-/isoamyl alcohol extractions, recovered by ethanol precipitation, and dried and resuspended in buffer.

Also preferred is the method in which the nucleic acid sequence is an RNA sequence. Preferably, the RNA sequence is an mRNA sequence. Additionally preferred is the method in which the RNA sequence is located in the cells of a tissue sample. An RNA sample containing the RNA sequence may be isolated using various methods for RNA isolation which are well-known to those of ordinary skill in the art. For example, an RNA sample may be isolated from cultured cells by washing the cells free of media and then lysing the cells by placing them in a 4M guanidinium solution. The viscosity of the resulting solution is reduced by drawing the lysate through a 20 gauge needle. The RNA is then pelleted through a $CsCl_2$ step gradient, and the supernatant fluid from the gradient carefully removed to allow complete separation of the RNA, found in the pellet, from contaminating DNA and protein.

The detectable marker useful for detecting a nucleic acid sequence coding for all or part of a trkC protein or a related nucleic acid sequence, may be a labeled DNA sequence, including a labeled cDNA sequence, having a nucleotide sequence complementary to at least a portion of the DNA sequence coding for all or part of a trkC protein.

The detectable marker may also be a labeled sense or antisense RNA sequence having a nucleotide sequence complementary to at least a portion of the DNA sequence coding for all or part of a trkC protein.

The detectable markers of the present invention may be labeled with commonly employed radioactive labels, such as $^{32}P$ and $^{35}S$, although other labels such as biotin or mercury may be employed. Various methods well-known to those of ordinary skill in the art may be used to label the detectable markers. For example, DNA sequences and RNA sequences may be labeled with $^{32}P$ or $^{35}S$, using the random primer method.

Once a suitable detectable marker has been obtained, various methods well-known to those of ordinary skill in the art may be employed for contacting the detectable marker with the sample of interest. For example, DNA-DNA, RNA-RNA and NDA-RNA hybridizations may be performed using standard procedures known in the art. In a typical DNA-DNA hybridization procedure for detecting DNA sequences coding for all or part of a trkC protein in genomic DNA, the genomic DNA is first isolated using known methods, and then digested with one or more restriction enzymes. The resulting DNA fragments are separated on agarose gels and denatured in situ. After prehybridization to reduce nonspecific hybridization, a radio-labeled nucleic acid probe is hybridized to the immobilized DNA fragments. The filter is then washed to remove unbound or weakly bound probe, and is then auto-radiographed to identify the DNA fragments that have hybridized with the probe.

The presence of bound detectable marker may be detected using various methods well-known to those of ordinary skill in the art. For example, if the detectable marker is radioactively labeled, autoradiography may be employed. Depending on the label employed, other detection methods such as spectrophotometry may also be used.

It should be understood that nucleic acid sequences related to nucleic acid sequences coding for all or part of a trkC protein can also be detected using the methods described herein. For example, a DNA probe based on conserved regions of a trkC protein can be used to detect and isolate related DNA sequences (e.g., a DNA sequence coding for a trkC protein from another organism). All such methods are included within the scope of the present invention.

As used in the present application and in this context, the term "related" means a nucleic acid sequence which is able to hybridize to an oligonucleotide probe based on the nucleotide sequence of a trkC protein.

The present invention further concerns polypeptide molecules comprising all or part of a trkC protein, said polypeptide molecules preferably having all or part of the amino acid sequence substantially as shown in FIG. 1B (SEQ. ID NO: 2).

The polypeptides of the present invention may be obtained by synthetic means, i.e., chemical synthesis of the polypeptide from its component amino acids, by methods known to those of ordinary skill in the art. For example, the solid phase procedure described by Houghton et al., Proc. Natl. Acad Sci. 82, 5135 (1985) may be employed. It is preferred that the polypeptides be obtained by production in prokaryotic or eukaryotic host cells expressing a DNA sequence coding for all or part of a trkC protein, or by in vitro translation of the mRNA encoded by a DNA sequence coding for all or part of a trkC protein. For example, the DNA sequence of FIG. 1B (SEQ. ID NO: 1) may be synthesized using PCR as described above and inserted into a suitable expression vector, which in turn may be used to transform a suitable host cell. The recombinant host cell may then be cultured to produce a trkC protein. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay or enzyme immunoassay. The antibodies may also be used in affinity chromatography for purifying the polypeptides of the present invention and isolating them from various sources.

The polypeptides of the present invention have been defined by means of determined DNA and deduced amino acid sequencing. Due to the degeneracy of the genetic code, other DNA sequences which encode the same amino acid sequence as depicted in FIG. 1B (SEQ. ID NO: 2) may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. Other contemplated variations include salts and esters of the afore-mentioned polypeptides, as well as precursors of the aforementioned polypeptides, for example, precursors having N-terminal substituents such as methionine, N-formylmethionine and leader sequences. All such variations are included within the scope of the present invention.

The following examples are further illustrative of the present invention. These examples are not intended to limit the scope of the present invention, and provide further understanding of the invention.

EXAMPLE 1

I. EXPERIMENTAL PROCEDURES

A. Isolation of cDNA Clones

A λgt 10 cDNA library ($1.5 \times 10^6$ phages) prepared from adult male porcine brain (Clontech Laboratories, Inc.) was plated on a lawn of *Escherichia coli* C 600 Hfl. Phages were absorbed onto nitrocellulose filters and lysed. Their DNAs were hybridized under relaxed conditions (48 hours at 42° C. in 5×SSC, 40% formamide, 1×Denhardt's solution and 10% dextran sulfate) with a nicktranslated $^{32}$P-labeled probe derived from the 1.2 kb BalI-EcoRI DNA fragment of pDM17 (ATCC 41055). This insert encompasses the entire tyrosine protein kinase catalytic domain of trk [Martin-Zanca, D. et al., Mol. Cell. Biol. 9, 24–33 (1989)]. Filters were washed three times at room temperature in 2×SSC, 0.1% SDS and once at 42° C. in 0.1×SSC, 0.1% SDS, and exposed 3 days at −70° C. with intensifying screens. The filters were then washed for 3 hours at 70° C. in 2.5 mM Tris pH 8.0, 0.1 mM EDTA, 0.025% sodium pyrophosphate and 0.001% Denhardt's solution.

The above library was rescreened under stringent conditions with nick-translated $^{32}$p-labeled probes derived from either pFRK46, a full length mouse trkB cDNA lacking the 3' untranslated region [See, Klein, R. et al., EMBO Journal 8, 3701–3709 (1989)] or pDM17. Phages showing strong hybridization signals to either of these probes were discarded. Those depicting weak hybridization were picked up and plague purified as described in Maniatis et al., supra. The inserts were subcloned into pBluescript.(Stratagene); the plasmid with the longest cDNA insert was designated pFL7.

A cDNA clone containing the 5' trkC sequence was isolated by rescreening the library with a nick-translated $^{32}$P-labeled probe (300 bp) generated by PCR, corresponding to the 5' end of pFL7, a partial cDNA clone containing part of the ligand binding region and the complete transmembrane and tyrosine kinase catalytic domains. This probe corresponds to sequences encoding the carboxy terminus of the extracellular domain and the entire transmembrane region of the porcine trkC product (nucleotides 1086–1600 in FIGS. 1B and 1C). In this case, the hybridization was performed under stringent conditions (48 hours at 42° C. in 5×SSC, 50% formamide, 1×Denhardt's solution and 10% dextran sulfate). The positive clone was plague purified as described previously (Maniatis et al., supra). Its 2.2 kb EcoRI insert was subcloned in pBluescript (Stratagene) to generate pFL15.

Mouse trkC cDNA clones were isolated from an adult mouse brain cDNA library [Citri M. et al., Nature 326, 42–47 (1987)]. $2 \times 10^6$ phages were plated on a lawn of *Escherichia coli* LE 392, absorbed onto nitrocellulose filters and hybridized under relaxed conditions (as described above) with a 315 bp Sal I $^{32}$P-labeled DNA fragment of pFL7. Positive phages were plaque purified as described in Maniatis et al., supra. A 2.4 kb EcoRI insert, the longest insert, was subcloned into pBluescript to generate pFL16. The partial nucleotide sequence (about 80% of sequence; the most 5' nucleotides are not shown) (SEQ. ID. NO.: 3) and the partial deduced amino acid sequence (about 80% of sequence; the most N-terminal amino acids are not shown) (SEQ. ID. NO.: 4) of the pFL16 insert is shown herein below.

Plasmid pFL16 was deposited with the American Type Culture Collection, Rockville, Md. on Jul. 3, 1991 under the Budapest Treaty and assigned ATCC accession no. 75045.

B. Nucleotide Sequencing

The 5' end of the cDNA sequence of pFL15 was assembled to the cDNA sequence of pFL7 using a unique Nae I site to generate pFL19. Sequencing was performed using the dideoxy chain termination method with double-stranded plasmid DNA, synthetic oligonucleotides and a modified T7 DNA polymerase (Sequenase; US Biochemicals).

C. Northern Blot Analysis

Total cellular RNA was prepared from adult tissue of Balb/c mice using the RNA zol TM method (CINNA/BIOTECX Lab. Int., Inc). The poly(A)-containing fraction was isolated by affinity chromatography on oligo (dT)-cellulose columns (Collaborative Research). 4 μg of poly (A) RNA were electrophoresed on a 1.2% agarose-formaldehyde gel, transferred to a nitrocellulose filter and hybridized under stringent conditions (48 hours at 42° C. in $5 \times$ ssc. 50% formamide, $1 \times$ Denhardt's and 10% dextran sulfate) with a 570 bp $^{32}$P-labeled Acc I fragment of pFL16 corresponding to a part of the external domain of mouse trkC. Hybridized filters were washed three times at room temperature for 15 minutes in $2 \times$ SSC, 0.1% SDS and once at 60° C. for 30 minutes in $0.1 \times$ SSC, 0.1% SDS, dried and exposed.

D. In Situ Hybridization

In situ hybridization analysis was performed as described (Hogan, B. L. M. et al., Manipulating the Mouse Embryo, Cold Spring Harbor Laboratory, Cold Spring Harbor, N.Y. (1986)). The 570 bp Acc I fragment of PFL16 was subcloned into pGEM-3Zf(+) (Promega) to generate pFL25. This Acc I insert corresponds to a part of the extracellular domain of mouse trkC.

In order to synthesize a $^{35}$S-labeled single-stranded antisense cRNA probe, pFL25 was linearized by digestion with Sac I and in vitro-transcribed with SP6 RNA polymerase (Promega), in the presence of $^{35}$S-labeled UTP (>1000 Ci/mmol, Dupont). Sagittal sections (5 μm thick) of 6–8 week adult mouse brain were mounted on superfrost plus glass slides (Fisher). Hybridization was performed under stringent conditions (16 hours at 52° C. in 50% formamide, $1 \times$ Denhardt's solution, 10% dextran sulfate, 0.5 mg/ml yeast RNA and 10 mM DTT) with the antisense RNA probes ($6 \times 10^5$ cpm). The slides were washed 30 minutes at 52° C. in $5 \times$ SSC, 10 mM DTT, then 20 minutes at 65° C. in a solution containing 50% formamide, $2 \times$ SSC and 10 mM DTT.

The sections were then incubated at 37° C. with RNAse A (20 μg/ml) and RNAse $T_1$ (2 pg/ml) for 1 hour and at 37° C. with 50% formamide, $2 \times$ SSC and 10 mm DTT for 3 hours. Finally the slides were washed in $2 \times$ SSC for 15 minutes at 37° C., then in $0.1 \times$ SSC for 15 minutes at 37° C. After dehydration, the slides were air dried, dipped into NTB-2 nuclear track emulsion (Kodak) and exposed for 7 days at 4° C. Control sections were hybridized with a $^{35}$S-labeled single-stranded sense cRNA probe transcribed from the T7-promoter of Sph I-linearized pFL25 DNA.

E. Expression Plasmids and Gene Transfer Assays

The 2,538 bp cDNA insert of pFL19 was subcloned into the mammalian expression vector pMEX-neo (Martin-Zanca, D. et al., Mol. Cell. Biol. 9, 24–33 (1989)]. The resulting plasmid, pFL20, was linearized by Aat II digestion.

Mouse NIH3T3 cells were transfected with the linearized plasmids according to the calcium phosphate precipitation technique to generate G418-resistant R4-31 cells (Graham, F. L. and van der Eb, A. J., Virology 52, 456–467 1973)].

F. Immunoprecipitation Analysis

Cells were metabolically labeled with $^{35}$S-labeled methionine (50 μCi/ml, 1,200 Ci/mmol, Amersham) for 3 hours in the absence or presence of tunicamycin (10 μg/ml). The immunoprecipitation analysis was performed as previously described (Martin-Zanca, D. et al., Mol. Cell. Biol. 9, 24–33 (1989)] using a polyclonal antibody (43-4) raised in rabbit against a synthetic peptide corresponding to the 14 carboxy-terminal residues of the deduced trk proto-oncogene sequence.

II. RESULTS

A. Molecular Cloning of trk cDNA Clones

An adult porcine brain cDNA library was screened with a probe corresponding to the catalytic domain of the human trk proto-oncogene under relaxed hybridization conditions. Over 100 recombinant phages were found to be positive. Filters containing these phages were rehybridized under stringent hybridization conditions with probes specific for either trk or trkB sequences (see Experimental Procedures above) in order to identify undesirable phage carrying trk or trkB cDNA inserts. Six positive clones that hybridized only weakly to these probes were isolated, and their EcoRI inserts subcloned in pBluescript vectors and submitted to further characterization. These six clones contained overlapping inserts ranging in size from 1.9 kbp to 2.3 kbp. Restriction enzyme analysis followed by partial nucleotide sequence analysis of these clones revealed that they were highly related to but distinct from the trk and trkB proto-oncogenes. Hybridization of genomic DNAs of porcine, mouse and human origin with a 320 bp ScaI-ApaI DNA fragment derived from these trk-related cDNA clones identified a series of DNA fragments that did not hybridize to probes derived from the corresponding regions of human trk and mouse trkB cDNA clones (data not shown). These results indicate that the above cDNA clones were not derived from the porcine trk or trkB locus. Therefore, they must correspond to transcripts encoded by a new trk-related gene, designated as trkC.

B. Nucleotide and Deduced Amino Acid Sequence of trk

None of the above clones contained sequences coding for the amino terminus of the putative trkC gene product. A small probe derived from the 5' end of the longest cDNA clone pFL7, was used to rescreen the porcine cDNA library. Only one recombinant phage carrying a 2.2 kbp EcoRI insert was identified. This insert, which extended furthest to the 5' end, was assembled with the pFL7 insert using a common Nae I site (FIG. 1A) to generate a single cDNA clone, pFL19. The nucleotide sequence of pFL19 is shown in FIG. 1B (SEQ. ID. NO.: 1). Nucleotides 1-31 are likely to represent 5' non-coding sequences. Nucleotides 32 to 2506 correspond to a long (2475 bp) open reading frame capable of coding for an 825 amino acid long polypeptide. The predicted ATG initiator codon conforms well with the canonical sequences of mammalian initiator codons. Moreover, the presence of an in-frame terminator (TAA, nucleotide 11-13) just upstream of the ATG, supports the concept that this codon represents the translational initiator of the trkC gene product. The last 20 nucleotides contain the terminator codon TAG and 17 3' untranslated residues. The small size of this region along with the absence of a polyadenylation signal suggests that pFL19 lacks a significant fraction of the 3' untranslated region of trkC transcript.

The deduced amino acid sequence of the porcine trkC protein encoded by FL19 is depicted in FIGS. 1B and 1C (SEQ. ID. NO.: 2). This 825 amino acid long polypeptide (93,129 daltons) exhibits the characteristic features of cell surface tyrosine protein kinases, including a signal peptide (positions 1 to 31), a long extracellular region encompassing 14 consensus N-glycosylation sites (Asn-X-Ser/Thr) (positions 32 to 429), a single transmembrane domain (positions 430 to 453) and a cytoplasmic region (positions 454 to 825) which includes the kinase catalytic domain (positions 544 to 810). The consensus sequence for the ATP binding motif is located at positions 545 to 572 [See, Hanks, S. K. et al., Science 241, 42–52 (1988)]. The trkC product, like the other two members of the trk gene family, has a very short carboxy terminal region of 15 amino acid residues which includes a conserved free tyrosine residue at the carboxy-terminus.

The overall homology of the trkC protein to the products of the human trk and mouse trkB proto-oncogene products is 67% and 68%, respectively. Their external domains exhibit 54% (trkC and trk) and 53% (trkC and trkB) similarities. Alignment of the deduced amino acid sequences of the three members of the mammalian trk gene family shows that the twelve external cysteine residues of the trkC product are present in the corresponding region of the trkB proteins and ten of them are shared with the trk gene product. Moreover, this alignment reveals a highly conserved region (residues 368–378 of the trkC sequence) which depicts an 82% identity among these three kinases. Interestingly, this sequence is part of the 51 amino acid long deletion responsible for the malignant activation of the trk5 oncogene [Oskam, R. et al., Proc. Natl. Acad. Sci. USA 85, 8913–8917 (1988); Coulier, F. et al., Mol. Cell. Biol. 10, 4202–4210 (1990)]. Therefore, this region may play an important role in regulating the catalytic activity of the internal kinase domain. Finally, the 267 amino acid long catalytic domain is 76% identical (87 homologous) to that of human trk and 83% identical (88% homologous) to that of the mouse trkB kinase. Much lower homologies were obtained when the sequence of the trkC protein was compared with other members of the cell surface tyrosine protein kinase family. The catalytic kinase region of the trkC product exhibits the characteristic features of the trk and trkB tyrosine kinases [Klein, R. et al., EMBO J. 8, 3701–3709 (1989); Martin-Zanca, D. et al., Mol. Cell. Biol. 9, 24–33 (1989)]. They include (i) a threonine residue (position 682) instead of the alanine present in all the other tyrosine protein kinases (with the exception of the putative tyrosine kinase JTK10 expressed in K562 human leukemia cells) (Partanen, J. et al., Proc. Natl. Acad. Sci. USA 87, 8913–8917 (1990)]; (ii) the putative autophosphorylation site, $Tyr^{709}$, is followed by a second tyrosine residue, a feature also present in the insulin receptor subfamily; (iii) a simple amino acid gap (between residues of 576 and 577); (iv) a tryptophane in position 757; and (v) the absence of a helix-breaking proline in position 801 [Hanks, S. K. et al., Science 241, 42–52 (1988)]. Finally, the trkC protein shares with the trk and trkB kinases their characteristic short carboxy-terminal tail. This 15 amino acid long region contains eight residues identical (12 homologous) to those of the trk and trkB kinases, including a tyrosine ($Tyr^{820}$) located five residues from the carboxy-terminus.

C. Identification of the trkC Product $gp140^{trkC}$

The pFL19 insert was next subcloned in the mammalian expression vector pMEXnec [Martin-Zanca, D. et al., Mol. Cell. Biol. 9, 24–33 (1989)], and the resulting plasmid, pFL20, used to transfect NIH3T3 cells. Several G418-resistant colonies were isolated and submitted to immunoprecipitation analysis using rabbit polyclonal antibodies elicited against a peptide corresponding to the 14 carboxy-terminal residues of the trk protein [Martin-Zanca, D. et al., Mol. Cel., Biol., 9, 24–33 (1989)]. As shown in FIG. 2 this antiserum recognized a major protein species with an apparent molecular weight of 145,000 likely to correspond to the mature trkC product (designated $gp145^{trkC}$). This molecular species is likely to be a glycoprotein since in the presence of tunicamycin, it exhibits a much faster electrophoretic mobility corresponding to a protein with a molecular weight of 90,000. This value corresponds well with the predicted size (93 kDa minus the signal peptide) for the polypeptide backbone of the trkC product. In addition to the $gp145^{trkC}$ protein, a smaller glycoprotein species of about 120,000 daltons was identified, and likely represents a partially glycosylated precursor. As expected, $gp145^{trkC}$ exhibited an in vitro kinase activity specific for tyrosine residues.

D. trkC is Expressed in the Central Nervous System

Figure 3A:
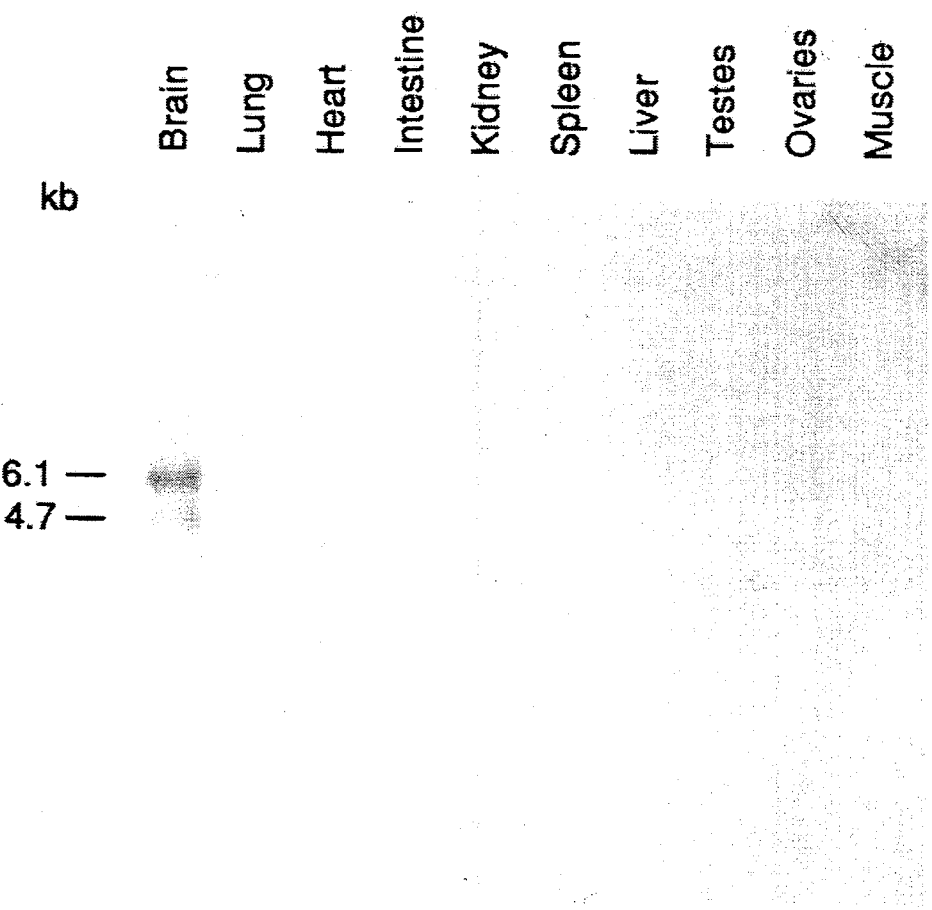
FIGS. 3A and 3B. Distribution of trkC transcripts in adult mouse tissues. (A) 4 μg of poly (A)-selected RNAs isolated from the indicated tissues were electrophoresed in a 1.2% agarose-formaldehyde gel, transferred to a nitrocellulose membrane and hybridized under stringent conditions (see Experimental Procedures) with a [$^{32}$P]-labeled 570 bp AccI DNA fragment of pFL16 mouse trkC cDNA clone corresponding to nucleotides 363-933 of pFL19 (see FIG. 1). (B) The same filter was hybridized with a [$^{32}$P]-labeled β-actin probe to control for the amount of RNA loaded in each lane. Hybridized blots were exposed to Kodak X-OMAT film at −70° C. with the help of intensifier screens for either (A) 15 days or (B) 8 hours. The sizes of the respective trkC and β-actin transcripts are indicated. RNA size markers included S. cerevisiae 28S and 18S and E. coli 23S and 16S ribosomal RNAs.
Figure 3B:
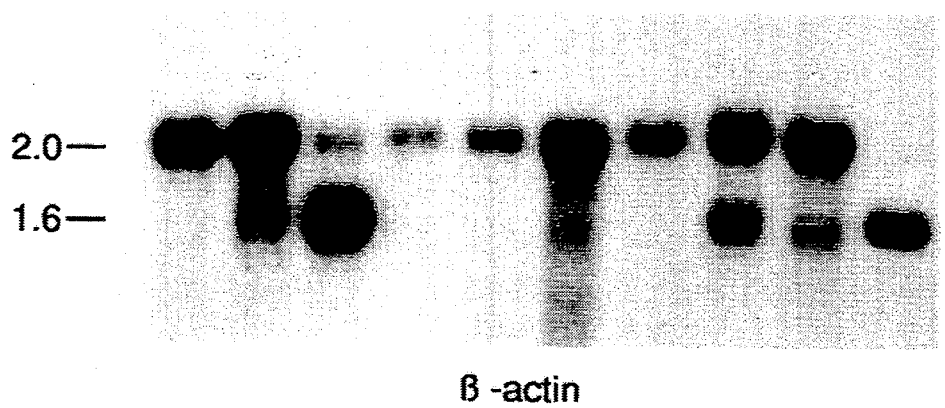

The above results indicated that trkC, along with trk and trkB, may constitute a subgroup of kinase receptors with structural as well as functional similarities. To examine this possibility, a series of adult mouse tissues were submitted to Northern blot analysis. To avoid possible cross-hybridization with other members of the trk gene family, a 2.4 kbp mouse trkC cDNA clone was isolated by screening a mouse brain cDNA library. As shown in FIG. 3, trkC transcripts of 6.1 kb and 4.7 kb can be readily detected in brain. However, all of the other tissues, with the possible exception of ovaries, lack detectable levels of trkC transcripts. These results suggest that the product of the trkC gene may also function as a neurogenic receptor.

Figure 4A:
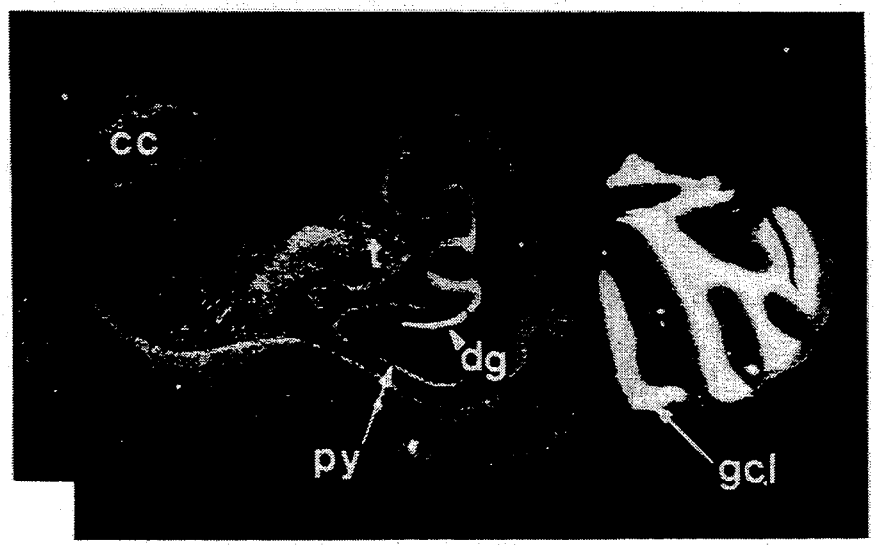
FIGS. 4A and 4B. trkC expression a mid-sagittal section of adult mouse brain. Dark field views of adjacent sections hybridized with (A) trkC-specific antisense cRNA probe and (B) trkC sense cRNA probe (see Experimental Procedures). (py) pyramidal cell layer of the hippocampus, (dg) dentate gyrus, (cc) cerebral cortex, (t) thalamus and (gcl) granular cell layer of the cerebellum.
Figure 4B:
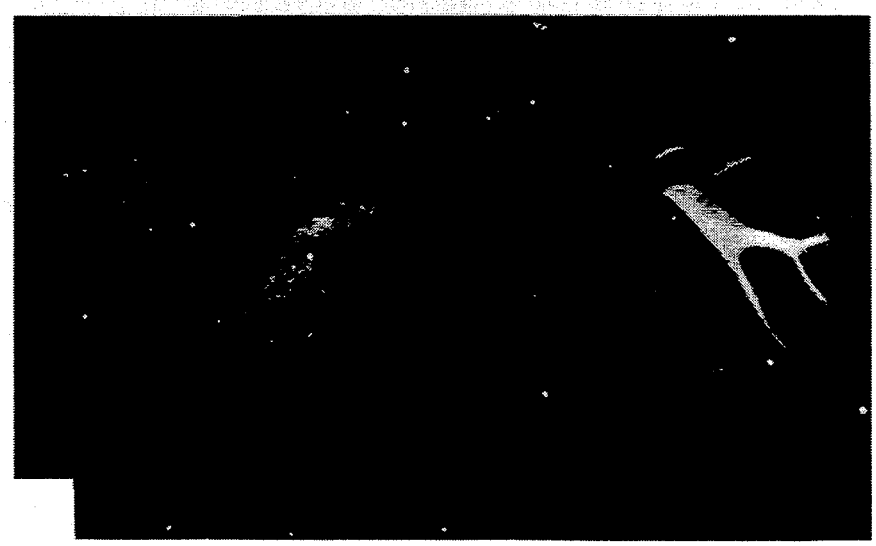

To determine the brain structures in which the trkC gene is expressed, preliminary in situ hybridization analysis of a mid-sagital section of an adult mouse brain was conducted. As shown in FIGS. 4A and 4B, a mouse trkC probe derived from the extracellular region readily hybridized to distinct structures including the pyramydal cell layer of the hippocampus, the dentate gyrus and external layers of the cerebral cortex. In addition, trkC transcripts were also identified in the specific regions of the cerebellum such as the granular cell layer. No detectable trkC expression could be observed in the white matter or in the Purkinje cell layer. These results indicate that trkC is primarily expressed in defined structures of the central nervous system.

EXAMPLE 2

I. Material and Methods

A. Isolation of trkC K1 and K2cDNA Clones

A trkC cDNA clone containing the 42 nucleotide-insert was isolated from an adult male porcine brain cDNA library (Clontech Laboratories, Inc.) by hybridization under relaxed conditions with a probe corresponding to the entire catalytic domain of the human trk proto-oncogene (1.2 Kb BaII-EcoRI fragment of pDMII) as described above and in Lamballe, F. et al., Cell 66, 967–979 (1991). Six phages exhibiting a weak hybridization were plague-purified and their EcoRI inserts subcloned into pBluescript (Stratagene) as described in Maniatis et al., supra. The EcoRI inserts were sequenced by the dideoxy chain termination method using double-stranded plasmid DNA, synthetic oligonucleotides and modified T7 DNA polymerase (Sequenase, USB). By comparing the sequence of the 6 cDNAs, we noticed that 1 contained an additional sequence of 42 nucleotides inserted in the region encoding the tyrosine kinase domain. This cDNA, a 2.3 Kb EcoRI fragment, was subcloned into pBluescript and was designated pFL6. pFL22 was generated by assembling pFL6 and pFL19 [plasmid containing sequences coding for the original trkC receptor, now designated trkC K1; see Example 1 above and Lamballe, F. et al., Cell 66, 967–979 (1991)] cDNAs using their unique SalI site.

Another new sequence encoding a protein designated trkC K3 was obtained from adult mouse brain cDNA by Polymerase Chain Reaction (PCR)-aided amplification. The 5′ amplimer was the oligonucleotide (SEQ. ID. NO: 5) 5′CACGAGGAATTCCCTGGTTGGAGCCAATCTACTAGTG-3′, which contains a created EcoRI site (underlined), and the 3′ amplimer was the oligonucleotide (SEQ. ID. NO: 6) 5′-CGAAGCTCTAGACATCACTCTCTGTGGTGAACTTCCGGTAC-3′which encompasses a created XbaI site (underlined). These amplimers correspond to sequences coding for the region neighboring the 42 nucleotide-insert described above. The PCR products were digested with EcoRI and XbaI then cloned into pBluescript. Three EcoRI/XbaI fragments were cloned (159 bp. 201 bp and 234 bp). Nucleotide sequence analysis was performed by using the dideoxy chain termination method and T3 and T7 primers of pBluescript. The 234 bp EcoRI/XbaI fragment subcloned into pBluescript was designated DFL28 and revealed to be a fragment of the tyrosine kinase domain of the mouse homolog of porcine trkC but also contained an additional sequence of 75 nucleotides inserted at the same position as the 42 nucleotide-insert of pFL22. The 234 bp DNA fragment of pFL28 was digested with the restriction enzymes AccI and FokI releasing a 143 bp DNA fragment which was then 5 inserted into the cDNA coding for the TrkC K1 receptor. The assembled cDNA was then subcloned into pMEXneo, a mammalian expression vector [(Martin-Zanca, D. et al., Mol Cell. Biol. 9, 24–33 (1989)] to generate pFL32.

B. Clonino of trkC NC1 and NC2 cDNA Clones

As described above and in Lamballe, F. et al., Cell 66, 967–979 (1991), an adult porcine brain cDNA library was screened with a probe corresponding to the 5′ end of the cDNA coding for the TrkC K1 receptor. Only 1 clone exhibited hybridization to this probe. This phage was plague purified. A 2.2 Kb EcoRI insert was identified and subcloned into pBluescript to generate DFL15. A mouse brain cDNA library (Citri, M. et al., Nature 326, 42–47 (1987)] was screened with a $^{32}$P-labeled 315 bp SalI DNA fragment corresponding to sequences encoding the 3′ region of the extracellular and the transmembrane domain. Six positive phages were picked. Their EcoRI inserts of size varying from 0.9 Kb to 2.5 Kb were subcloned into pBluescript. Restriction digest of the plasmid containing the 2.5KD ECoRZ insert revealed a pattern different from the other clones identified as trkC. This plasmid was designated pFhL18. The nucleotide sequence of pFL15 and pFL18 was determined by the dideoxy chain termination method using T3 and T7 primers, synthetic oligonucleotides and modified T7 DNA polymerase (Sequenase, USB).

C. Expression Plasmids and Cells

NIH3T3-derived cell lines including G4-6-11, G4-8-11 and FL12-3-6 were generated by transfecting respectively pFL20 (TrkC K1), pFL23 (TrkC K2) and pFL32 (TrkC K3) using the calcium phosphate precipitation technique as described in Graham, F. L. and van der Eb, A. J., Virology 52,456–467 (1973). The expression plasmid, pFL20, was generated by subcloning TrkC K1 cDNA into the mammalian expression vector pMEXneo as described above and in Lamballe, F. et al., Cell 9, 967–979 (1991). pFL23 is a pMEXneo-derived expression plasmid encoding the TrkC K2 receptor. In order to generate pFL23, the 2568 bp EcoRI fragment of pFL22, corresponding to the full length TrkC K2 cDNA, was subcloned into the mammalian expression vector pMEX-neo (Martin-Zanca, Det al., Mol. Cell. Biol. 9, 24–33 (1989)]. pFL32, the expression plasmid encoding the TrkC K3 receptor, is described above.

II. RESULTS

A. Multiple TrkC Tyrosine Protein Kinase Receptors we have previously described the isolation of a new member of the trk gene family, designated trkC and now designated trkC K1 (see above and Lamballe, F. et al., Cell 66, 967–979 (1991)]. During the course of this study, we also isolated a second trkC cDNA (pFL6) which included an additional sequence of 42 nucleotides inserted in the region coding for the tyrosine kinase domain, between nucleotides corresponding to codons 711 and 712 of the previously report trkC coding sequences (between nucleotides 2164–2165 of pFL19, a plasmid containing a 2526 bp cDNA insert encompassing the entire coding region of the porcine trkC gene [see above and Lamballe, F. et al., Cell 66, 967–979 (1991)]. The rest of the pFL6 cDNA clone was found to be identical to pFL19. These observations suggest the existence of a second TrkC receptor with 14 additional amino acid residues in the catalytic tyrosine kinase domain (See FIG. 5). More specifically, these residues are located at the end of subdomain VII [Hanks, S. K. et al., Science 245, 42–52 (1988)], following the YYR motif characteristic of the insulin receptor subfamily, where the first tyrosine is thought to correspond to the autophosphorlation site of the Src kinase. We have decided to designate this putative TrkC receptor isoform as TrkC K2. The previously characterized TrkC receptor gp 145$^{trkc}$ (See above and in Lamballe, F. et al., Cell 66, 967–979 (1991)], will now be designated as TrkC K1 (See FIGS. 1A to 1C).

To eliminate the possibility that the 42 nucleotide insert of pFL6 was a cloning artifact, we performed a Polymerase Chain Reaction (PCR)-aided amplification of total adult mouse brain cDNA using amplimers flanking the insert region. Parallel PCR amplifications were performed on pFL19 and pFL6 as controls. As shown in FIG. 5, the amplified DNA contained three distinct DNA fragments. Two of these fragments corresponded to the sizes expected for sequences amplified from cDNAs encoding TrkC K1 (159 bp) and TrkC K2 (201 bp) receptor isoforms. The third PCR product exhibited an electrophoretical mobility corresponding to a DNA fragment of about 240 bp, suggesting the presence of a novel trkC cDNA carrying additional coding sequences (FIG. 5).

To investigate the nature to these PCR products, they were subcloned into pBluescript and representative clones submitted to nucleotide sequence analysis. All clones derived from the smalles DNA fragment exhibited the expected sequences for the previously described TrkC K1 (gp145$^{trkC}$; see above and Lamballe. F. et al., Cell 66, 967–979 (1991)]. Likewise, the middle size DNA fragment yielded colonies whose sequences were identical to those present in pFL6 and therefore correspond to transcripts encoding the putative TrkC K2 receptor isoform. Clones derived from a larger PCR product encompassed sequences derived from the same region of the trkC gene, but contained an additional stretch of 75 nucleotides inserted at the same position (between pFL19 codons 710 and 711) as the 42 nucleotide insert of pFL6. These observations suggest the existence of a third TrkC receptor isoform which we have designated as TrkC K3. A schematic representation of these putative TrkC tyrosine kinase receptors is depicted in FIG. 5.

From the above discussion, it can be seen that the DNA sequence encoding porcine TrkC K2 is the same as shown in FIG. 1B with the addition of the following DNA sequence between nucleotides 2164 and 2165: CTCTTTAATCCATCTGGAAATGATTTTTGTATATGGTGTGAG The amino acid sequence of porcine TrkC K2 is the same as shown in FIG. 1B with the addition of the 14 amino acids shown in FIG. 5B between amino acids 711 and 712. The partial DNA sequence encoding and the deduced amino acid sequence of murine TrkC K2 is shown in SEQ. ID NO: 3 and SEQ. ID NO: 4, respectively. The partial DNA sequence encoding murine TrkC K3 is the same as shown in SEQ. ID NO: 3 except that nucleotides 1801 to 1842 have been replaced with the following sequence (SEQ ID NO: 8): GAAGGGCCATGCCAGAAGGGCCCATTCAACGTGTCGTGGCAGCAGCAGAGG CTAGCAGCGTCAGCAGCTTCCACA. The partial amino acid sequence of murine TrkC K3 is the same as shown in SEQ ID NO: 4 except that amino acids 601 to 614 have been replaced with the 25 amino acids shown in FIG. 5C. The partial DNA sequence encoding murine TrkC K1 is the same as shown in SEQ. ID NO: 3 except that nucleotides 1801 to 1842 are deleted. The partial amino acid sequence of murine TrkC K1 is the same as shown in SEQ. ID NO: 4 except that amino acids 601 to 614 are deleted.

B. Non-catalytic TrkC Receptor Isoforms

In addition to the novel catalytic isoforms of the TrkC receptor described above, we have identified two cDNAs encoding putative non-catalytic TrkC receptors similar to the previously described gp95$^{trkB}$ protein [Klein, R. et al., Cell 61, 647–656 (1990)]. Screening of the same adult porcine brain cDNA library that yielded pFL6 with a probe corresponding to the 5' end pF19, revealed a novel 2181 bp long cDNA clone, pFL15, which lacks those sequences encoding the tyrosine kinase catalytic domain. Nucleotides 1 to 1480 of pFL15 are identical to those present in pFL19 [Lamballe, F. et al., Cell 66, 967–979 (1991)]. They correspond to those coding for the extracellular and transmembrane domains as well as the first 30 amino acids of the cytoplasmic region of the TrkC K1 receptor. However, the homology between pFL15 and PFL19 stops at nucleotide 1481. pFL15 exhibits an unrelated nucleotide sequence capable of encoding 21 additional amino acid residues followed by an in-frame terminator codon (TAG) (FIG. 5). The putative receptor encoded by this cDNA clone has been designated as TrkC NC1 where NC stands for "non-catalytic". No homology could be found between the unique 21 amino acid residues of TrkC NC1 with any of the three Trk kinase receptors. The 3' untranslated region of pFL15 (nucleotides 1546 to 2181) was also found to be unrelated to the previously characteriaed trkC cDNA clones (FIG. 5).

Screening an adult mouse brain cDNA library with a probe derived from the 5' region of the porcine pFL19 cDNA clone revealed several cDNA clones capable of coding for a putative second non-catalytic TrkC receptor isoform, designated TrkC Nc2. The longest cDNA clone. pFL18, contained a cDNA insert of 2,300 bp of which nucleotides 1 to 1066 exhibited extensive homology with those sequences of the porcine pFL19 cDNA clone (nucleotides corresponding to codons 112 to 466) encoding the carboxy-terminal half of the extracellular domain, the transmembrane region and the first 13 amino acid residues of the cytoplasmic domain. However, as indicated above with the porcine pFL15 cDNA clone, nucleotides 1077 to 2300 of the mouse pFL18 cDNA clone were unrelated to all porcine cDNA clones. These unique sequences encoded a 36 amino acid sequence followed by an in-frame TAA terminator codon. These 36 amino acid residues display no homology to any of the previously described TrkC receptor isoforms. A schematic representation of these non-catalytic TrkC receptors, TrkC NC1 and TrkC NC2, is depicted in FIG. 5.

From the above discussion, it can be seen that the DNA sequence encoding porcine TrkC NC1 consists of nucleotides 1–1480 as shown in FIG. 1B, but instead of nucleotides 1481–2526, the following DNA sequence is (SEQ ID NO. 9) present: ATCAACCATGGCATCACCACACCCTCATCACTGGACGCCGGGCCGGACACA GTGTCATTGGCATGA. The amino acid sequence of porcine TrkC NC1 consists of amino acids 1–483 as shown in FIG. 1B, but instead of amino acids 484–825, the amino acid sequence shown in FIG. 5E is present. The partial DNA sequence encoding murine TrkC NC2 consists of nucleotides 1–1065 as shown in SEQ. ID NO: 3, but instead of nucleotides 1066–2376, the following DNA sequence (SEQ. ID. NO: 10) is present: AAGGTGTTGTTTTTTCAGTCCCAAGAGTTCCATGGTTCCACCTATTGATC AAAAGATACTGTACCTCCATATGGTCTCTGCGAAAGCCTTTGGTCACTGGA CCTTGGTAA. The partial amino acid sequence of murine TrkC NC2 consists of amino acids 1–355 as shown in SEQ. ID NO: 4, but instead of amino acids 356–728, the amino acid sequence shown in FIG. 5D is present.

---

We claim:

1. An isolated nucleic acid molecule coding for a trkC protein wherein said nucleic acid is selected from the group consisting of:
   (a) a nucleic acid comprising a nucleic acid sequence coding for the amino acid sequence of FIGS 1B and 1C (SEQ. ID. NO.:2) and
   (b) a nucleic acid capable of hybridizing to the complement of a nucleic acid according to (a) above under stringent conditions.

2. The nucleic acid molecule according to claim 1 which is a DNA molecule and wherein the nucleic acid sequence is a DNA sequence.

3. The DNA molecule according to claim 2 wherein the encoded trkC protein is TrkC K1, TrkC K2, TrkC K3, TrkC NC1 or TrkC NC2.

4. The DNA molecule according to claim 2 wherein the DNA sequence has the nucleotide sequence as shown in FIG. 1B (SEQ. ID NO: 1).

5. The DNA molecule according to claim 2 wherein the DNA sequence has the nucleotide sequence of the 2.4 kb EcoRI insert of pFL16 deposited with the American Type Culture Collection.

6. A DNA molecule having a DNA sequence which is complementary to the DNA sequence according to claims 4 or 5.

7. An expression vector comprising a DNA coding for a trkC protein wherein said DNA is selected from the group consisting of:
   (a) a DNA having a sequence coding for the amine acid sequence of FIGS. 1B and 1C (SEQ. ID. NO.: 2) and
   (b) a DNA capable of hybridizing to the complement of a DNA according to (a) above under stringent conditions.

8. The expression vector according to claim 7 comprising one or more control DNA sequences capable of directing the replication and/or the expression of and operatively linked to the DNA coding for a trkC protein.

9. The expression vector according to claim 7 wherein the DNA coding for a trkC protein has the nucleotide sequence substantially as shown in FIG. 1B (SEQ. ID NO: 1).

10. The expression vector according to claim 7 wherein the DNA sequence coding for the amino acid sequence of FIGS. 1B and 1C (SEQ. ID. NO.: 2) has the nucleotide sequence shown in FIGS. 1B and 1C (SEQ. ID NO: 1).

11. The expression vector according to claim 7 wherein the DNA coding for a trkC protein has the nucleotide sequence of the 2.4 kb EcoRI insert of pFL16 deposited with the American Type Culture Collection.

12. The expression vector according to claim 7 designated pFL19.

13. The expression vector according to claim 7 designated pFL16.

14. The expression vector according to claim 7 wherein the encoded trkC protein is TrkC K1, TrkC K2, TrkC K3, TrkC NC1 or TrkC NC2.

15. A prokaryotic or eukaryotic host cell containing the expression vector according to claim 8, 9, 10, 11, 12, 13 or 14.

16. A prokaryotic or eukaryotic host cell containing the expression vector according to claim 7.

17. A method for producing a polypeptide molecule which comprises a trkC protein comprising culturing a host cell according to claim 16 under conditions permitting expression of the polypeptide molecule.

18. A method for detecting a nucleic acid encoding all or part of a trkC protein or a related nucleic acid comprising contacting the nucleic acid with a detectable marker having a sequence of at least 15 sequential nucleotides complementary to the nucleic acid sequence of FIGS. 1B and 1C (SEQ. ID. NO.: 1 ) under conditions which permit binding of said nucleic acid to said marker and detecting the marker so bound, the presence of bound marker indicating the presence of the nucleic acid.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 2526 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 32..2506

( x i ) SEQUENCE DESCRIPTION: SEQ ID NO:1:

```
CGGGCTCCGA TAACCGAAGC AGCGATCGGA G ATG GAT GTC TCT CTT TGC CCA            52
                                   Met Asp Val Ser Leu Cys Pro
                                    1               5

GCC AAG TCT AGT TTC TGG CGG ATT TTC TTG CTG GGA AGC GTC TGG CTG          100
Ala Lys Ser Ser Phe Trp Arg Ile Phe Leu Leu Gly Ser Val Trp Leu
         10                  15                  20

GAC TAT GTG GGC TCC GTG CTG GCT TGC CCT GCA AAT TGT GTC TGC AGC          148
Asp Tyr Val Gly Ser Val Leu Ala Cys Pro Ala Asn Cys Val Cys Ser
             25                  30                  35

AAG ACT GAG ATC AAT TGC CGG CGG CCG GAC GAT GGG AAC CTC TTC CCC          196
Lys Thr Glu Ile Asn Cys Arg Arg Pro Asp Asp Gly Asn Leu Phe Pro
 40                  45                  50                  55

CTC CTG GAA GGG CAG GAT TCA GGG AAC AGC AAT GGG AAT GCC AGC ATC          244
Leu Leu Glu Gly Gln Asp Ser Gly Asn Ser Asn Gly Asn Ala Ser Ile
                 60                  65                  70

AAC ATC ACG GAC ATC TCA AGG AAT ATC ACT TCC ATA CAC ATA GAG AAC          292
Asn Ile Thr Asp Ile Ser Arg Asn Ile Thr Ser Ile His Ile Glu Asn
             75                  80                  85

TGG CGC GGT CTG CAC ACG CTC AAC GCT GTG GAC ATG GAG CTC TAC ACC          340
Trp Arg Gly Leu His Thr Leu Asn Ala Val Asp Met Glu Leu Tyr Thr
         90                  95                 100

GGC CTC CAG AAG CTG ACC ATC AAG AAC TCA GGA CTT CGG AGC ATC CAG          388
Gly Leu Gln Lys Leu Thr Ile Lys Asn Ser Gly Leu Arg Ser Ile Gln
    105                 110                 115

CCC AGA GCC TTT GCC AAG AAC CCC CAC CTG CGC TAC ATA AAC CTG TCG          436
Pro Arg Ala Phe Ala Lys Asn Pro His Leu Arg Tyr Ile Asn Leu Ser
120                 125                 130                 135

AGT AAC CGG CTC ACC ACA CTC TCA TGG CAG CTC TTC CAG ACG CTG AGT          484
Ser Asn Arg Leu Thr Thr Leu Ser Trp Gln Leu Phe Gln Thr Leu Ser
                140                 145                 150

CTT CGG GAA TTG AGA TTG GAG CAG AAC TTC TTC AAC TGC AGC TGT GAC          532
Leu Arg Glu Leu Arg Leu Glu Gln Asn Phe Phe Asn Cys Ser Cys Asp
            155                 160                 165

ATC CGC TGG ATG CAG CTG TGG CAG GAG CAG GGG GAG GCC AAG CTG AAC          580
Ile Arg Trp Met Gln Leu Trp Gln Glu Gln Gly Glu Ala Lys Leu Asn
        170                 175                 180
```

| | | | | | | | | | | | | | | | | |
|---|---|---|---|---|---|---|---|---|---|---|---|---|---|---|---|---|
| AGC | CAG | AGC | CTC | TAT | TGC | ATC | AGT | GCC | GAT | GGC | TCC | CAG | CTC | CCC | CTC | 628 |
| Ser | Gln | Ser | Leu | Tyr | Cys | Ile | Ser | Ala | Asp | Gly | Ser | Gln | Leu | Pro | Leu | |
| 185 | | | | | 190 | | | | | 195 | | | | | | |
| TTC | CGC | ATG | AAC | ATT | AGC | CAG | TGT | GAC | CTT | CCT | GAG | ATC | AGT | GTG | AGC | 676 |
| Phe | Arg | Met | Asn | Ile | Ser | Gln | Cys | Asp | Leu | Pro | Glu | Ile | Ser | Val | Ser | |
| 200 | | | | | 205 | | | | | 210 | | | | | 215 | |
| CAC | GTC | AAT | CTG | ACC | GTT | CGG | GAG | GGT | GAC | AAT | GCT | GTT | GTC | ACC | TGC | 724 |
| His | Val | Asn | Leu | Thr | Val | Arg | Glu | Gly | Asp | Asn | Ala | Val | Val | Thr | Cys | |
| | | | | 220 | | | | 225 | | | | | 230 | | | |
| AAT | GGC | TCT | GGA | TCA | CCC | CTG | CCC | GAC | GTG | GAC | TGG | ATC | GTC | ACT | GGA | 772 |
| Asn | Gly | Ser | Gly | Ser | Pro | Leu | Pro | Asp | Val | Asp | Trp | Ile | Val | Thr | Gly | |
| | | | 235 | | | | 240 | | | | | 245 | | | | |
| CTG | CAG | TCC | ATC | AAC | ACC | CAC | CAG | ACA | AAT | CTG | AAT | TGG | ACC | AAC | GTA | 820 |
| Leu | Gln | Ser | Ile | Asn | Thr | His | Gln | Thr | Asn | Leu | Asn | Trp | Thr | Asn | Val | |
| | | 250 | | | | 255 | | | | | 260 | | | | | |
| CAC | GCC | ATC | AAC | CTG | ACA | CTG | GTC | AAT | GTG | ACG | AGT | GAG | GAC | AAC | GGC | 868 |
| His | Ala | Ile | Asn | Leu | Thr | Leu | Val | Asn | Val | Thr | Ser | Glu | Asp | Asn | Gly | |
| | 265 | | | | 270 | | | | | 275 | | | | | | |
| TTC | ACC | CTG | ACG | TGC | ATT | GCA | GAG | AAC | GTG | GTG | GGC | ATG | AGC | AAT | GCC | 916 |
| Phe | Thr | Leu | Thr | Cys | Ile | Ala | Glu | Asn | Val | Val | Gly | Met | Ser | Asn | Ala | |
| 280 | | | | | 285 | | | | | 290 | | | | | 295 | |
| AGC | GTC | GCC | CTC | ACT | GTT | CAC | TAC | CCC | CCA | CGA | GTG | GTG | AGC | CTG | GAG | 964 |
| Ser | Val | Ala | Leu | Thr | Val | His | Tyr | Pro | Pro | Arg | Val | Val | Ser | Leu | Glu | |
| | | | | 300 | | | | 305 | | | | | 310 | | | |
| GAG | CCA | GAG | CTG | CGC | CTG | GAA | CAC | TGC | ATC | GAG | TTT | GTG | GTG | CGT | GGC | 1012 |
| Glu | Pro | Glu | Leu | Arg | Leu | Glu | His | Cys | Ile | Glu | Phe | Val | Val | Arg | Gly | |
| | | | 315 | | | | 320 | | | | | 325 | | | | |
| AAC | CCG | CCG | CCC | ACG | CTG | CAC | TGG | CTG | CAC | AAC | GGG | CAG | CCG | CTG | CGT | 1060 |
| Asn | Pro | Pro | Pro | Thr | Leu | His | Trp | Leu | His | Asn | Gly | Gln | Pro | Leu | Arg | |
| | | 330 | | | | 335 | | | | | 340 | | | | | |
| GAG | TCC | AAG | ATC | ACC | CAC | GTG | GAG | TAC | TAC | CAG | GAG | GGC | GAG | GTC | TCC | 1108 |
| Glu | Ser | Lys | Ile | Thr | His | Val | Glu | Tyr | Tyr | Gln | Glu | Gly | Glu | Val | Ser | |
| | 345 | | | | 350 | | | | | 355 | | | | | | |
| GAG | GGC | TGC | CTG | CTC | TTC | AAC | AAG | CCC | ACC | CAC | TAC | AAC | AAT | GGC | AAC | 1156 |
| Glu | Gly | Cys | Leu | Leu | Phe | Asn | Lys | Pro | Thr | His | Tyr | Asn | Asn | Gly | Asn | |
| 360 | | | | | 365 | | | | | 370 | | | | | 375 | |
| TAC | ACA | CTC | AAT | CGC | CAA | GAA | CCC | CTT | GGC | ACA | GCC | AAC | CAG | ACC | ATC | 1204 |
| Tyr | Thr | Leu | Asn | Arg | Gln | Glu | Pro | Leu | Gly | Thr | Ala | Asn | Gln | Thr | Ile | |
| | | | | 380 | | | | 385 | | | | | 390 | | | |
| AAT | GGC | CAC | TTC | CTC | AAG | GAG | CCT | TTT | CCA | GAG | AGC | ACG | GAT | AAC | TTT | 1252 |
| Asn | Gly | His | Phe | Leu | Lys | Glu | Pro | Phe | Pro | Glu | Ser | Thr | Asp | Asn | Phe | |
| | | | 395 | | | | 400 | | | | | 405 | | | | |
| GTC | TCT | TTC | TAT | GAA | GTG | AGC | CCC | ACC | CCT | CCC | ATC | ACT | GTG | ACG | CAC | 1300 |
| Val | Ser | Phe | Tyr | Glu | Val | Ser | Pro | Thr | Pro | Pro | Ile | Thr | Val | Thr | His | |
| | | | 410 | | | | 415 | | | | | 420 | | | | |
| AAG | CCA | GAG | GAA | GAT | ACA | TTT | GGG | GTA | TCC | ATA | GCT | GTT | GGA | CTT | GCC | 1348 |
| Lys | Pro | Glu | Glu | Asp | Thr | Phe | Gly | Val | Ser | Ile | Ala | Val | Gly | Leu | Ala | |
| | 425 | | | | 430 | | | | | 435 | | | | | | |
| GCT | TTT | GCC | TGT | GTC | CTT | CTG | GTG | GTT | CTC | TTT | ATC | ATG | ATC | AAC | AAG | 1396 |
| Ala | Phe | Ala | Cys | Val | Leu | Leu | Val | Val | Leu | Phe | Ile | Met | Ile | Asn | Lys | |
| 440 | | | | | 445 | | | | | 450 | | | | | 455 | |
| TAT | GGT | CGA | CGG | TCT | AAA | TTT | GGA | ATG | AAG | GGT | CCT | GTG | GCT | GTC | ATC | 1444 |
| Tyr | Gly | Arg | Arg | Ser | Lys | Phe | Gly | Met | Lys | Gly | Pro | Val | Ala | Val | Ile | |
| | | | | 460 | | | | 465 | | | | | 470 | | | |
| AGT | GGT | GAA | GAG | GAC | TCA | GCC | AGC | CCA | CTG | CAT | CAC | GAT | CAA | CCA | TGG | 1492 |
| Ser | Gly | Glu | Glu | Asp | Ser | Ala | Ser | Pro | Leu | His | His | Asp | Gln | Pro | Trp | |
| | | | 475 | | | | 480 | | | | | 485 | | | | |
| CAT | CAC | CAC | ACC | CTC | ATC | ACT | GGA | CGC | CGG | GCC | GGA | CAC | AGT | GTC | ATT | 1540 |
| His | His | His | Thr | Leu | Ile | Thr | Gly | Arg | Arg | Ala | Gly | His | Ser | Val | Ile | |
| | | | | 490 | | | | 495 | | | | | 500 | | | |
| GGC | ATG | ACC | CGC | ATC | CCA | GTC | ATT | GAG | AAC | CCC | CAG | TAC | TTC | CGC | CAG | 1588 |

-continued

| | | | | | | | | | | | | | | |
|---|---|---|---|---|---|---|---|---|---|---|---|---|---|---|
|Gly|Met|Thr|Arg|Ile|Pro|Val|Ile|Glu|Asn|Pro|Gln|Tyr|Phe|Arg|Gln|
| |505| | | |510| | | | |515| | | | |

| GGA | CAC | AAC | TGC | CAC | AAG | CCA | GAC | ACG | TAT | GTG | CAG | CAC | ATT | AAA | AGG | 1636 |
|---|---|---|---|---|---|---|---|---|---|---|---|---|---|---|---|---|
| Gly | His | Asn | Cys | His | Lys | Pro | Asp | Thr | Tyr | Val | Gln | His | Ile | Lys | Arg | |
| 520 | | | | 525 | | | | | 530 | | | | | 535 | | |

| AGG | GAC | ATC | GTG | CTG | AAG | CGA | GAA | CTG | GGT | GAG | GGA | GCC | TTT | GGG | AAG | 1684 |
|---|---|---|---|---|---|---|---|---|---|---|---|---|---|---|---|---|
| Arg | Asp | Ile | Val | Leu | Lys | Arg | Glu | Leu | Gly | Glu | Gly | Ala | Phe | Gly | Lys | |
| | | | | 540 | | | | | 545 | | | | | 550 | | |

| GTC | TTC | CTG | GCC | GAG | TGC | TAC | AAC | CTC | AGC | CCC | ACC | AAG | GTC | AAG | ATG | 1732 |
|---|---|---|---|---|---|---|---|---|---|---|---|---|---|---|---|---|
| Val | Phe | Leu | Ala | Glu | Cys | Tyr | Asn | Leu | Ser | Pro | Thr | Lys | Val | Lys | Met | |
| | | | 555 | | | | | 560 | | | | | 565 | | | |

| CTC | GTG | GCT | GTG | AAG | GCC | CTG | AAG | GAT | CCC | ACC | CTG | GCC | GCC | CGG | AAG | 1780 |
|---|---|---|---|---|---|---|---|---|---|---|---|---|---|---|---|---|
| Leu | Val | Ala | Val | Lys | Ala | Leu | Lys | Asp | Pro | Thr | Leu | Ala | Ala | Arg | Lys | |
| | | 570 | | | | | 575 | | | | | 580 | | | | |

| GAT | TTC | CAG | AGG | GAG | GCT | GAG | CTG | CTC | ACC | AAC | CTG | CAG | CAT | GAG | CAC | 1828 |
|---|---|---|---|---|---|---|---|---|---|---|---|---|---|---|---|---|
| Asp | Phe | Gln | Arg | Glu | Ala | Glu | Leu | Leu | Thr | Asn | Leu | Gln | His | Glu | His | |
| 585 | | | | | 590 | | | | | 595 | | | | | | |

| ATT | GTC | AAG | TTC | TAT | GGG | GTG | TGC | GGC | GAC | GGG | GAC | CCA | CTC | ATC | ATG | 1876 |
|---|---|---|---|---|---|---|---|---|---|---|---|---|---|---|---|---|
| Ile | Val | Lys | Phe | Tyr | Gly | Val | Cys | Gly | Asp | Gly | Asp | Pro | Leu | Ile | Met | |
| 600 | | | | | 605 | | | | | 610 | | | | | 615 | |

| GTT | TTT | GAG | TAC | ATG | AAA | CAC | GGG | GAT | CTG | AAC | AAG | TTC | CTC | AGG | GCC | 1924 |
|---|---|---|---|---|---|---|---|---|---|---|---|---|---|---|---|---|
| Val | Phe | Glu | Tyr | Met | Lys | His | Gly | Asp | Leu | Asn | Lys | Phe | Leu | Arg | Ala | |
| | | | | 620 | | | | | 625 | | | | | 630 | | |

| CAG | GGG | CCA | GAT | GCC | ATG | ATC | CTC | GTG | GAC | GGC | CAG | CCA | CGC | CAG | GCA | 1972 |
|---|---|---|---|---|---|---|---|---|---|---|---|---|---|---|---|---|
| Gln | Gly | Pro | Asp | Ala | Met | Ile | Leu | Val | Asp | Gly | Gln | Pro | Arg | Gln | Ala | |
| | | | 635 | | | | | 640 | | | | | 645 | | | |

| AAA | GGC | GAG | CTG | GGG | CTC | TCC | CAG | ATG | CTG | CAC | ATT | GCC | AGT | CAG | ATC | 2020 |
|---|---|---|---|---|---|---|---|---|---|---|---|---|---|---|---|---|
| Lys | Gly | Glu | Leu | Gly | Leu | Ser | Gln | Met | Leu | His | Ile | Ala | Ser | Gln | Ile | |
| | | 650 | | | | | 655 | | | | | 660 | | | | |

| TGC | TCT | GGC | ATG | GTG | TAC | CTG | GCC | TCC | CAG | CAT | TTT | GTG | CAC | CGG | GAC | 2068 |
|---|---|---|---|---|---|---|---|---|---|---|---|---|---|---|---|---|
| Cys | Ser | Gly | Met | Val | Tyr | Leu | Ala | Ser | Gln | His | Phe | Val | His | Arg | Asp | |
| | 665 | | | | | 670 | | | | | 675 | | | | | |

| CTG | GCC | ACC | AGG | AAC | TGC | CTG | GTT | GGA | GCC | AAC | CTG | CTG | GTG | AAG | ATT | 2116 |
|---|---|---|---|---|---|---|---|---|---|---|---|---|---|---|---|---|
| Leu | Ala | Thr | Arg | Asn | Cys | Leu | Val | Gly | Ala | Asn | Leu | Leu | Val | Lys | Ile | |
| 680 | | | | | 685 | | | | | 690 | | | | | 695 | |

| GGC | GAT | TTC | GGC | ATG | TCC | AGA | GAT | GTC | TAC | AGC | ACG | GAT | TAC | TAC | AGG | 2164 |
|---|---|---|---|---|---|---|---|---|---|---|---|---|---|---|---|---|
| Gly | Asp | Phe | Gly | Met | Ser | Arg | Asp | Val | Tyr | Ser | Thr | Asp | Tyr | Tyr | Arg | |
| | | | | 700 | | | | | 705 | | | | | 710 | | |

| GTA | GGA | GGA | CAC | ACC | ATG | CTC | CCA | ATT | CGC | TGG | ATG | CCT | CCT | GAA | AGC | 2212 |
|---|---|---|---|---|---|---|---|---|---|---|---|---|---|---|---|---|
| Val | Gly | Gly | His | Thr | Met | Leu | Pro | Ile | Arg | Trp | Met | Pro | Pro | Glu | Ser | |
| | | | 715 | | | | | 720 | | | | | 725 | | | |

| ATC | ATG | TAC | CGG | AAG | TTC | ACT | ACT | GAG | AGT | GAC | GTG | TGG | AGC | TTC | GGG | 2260 |
|---|---|---|---|---|---|---|---|---|---|---|---|---|---|---|---|---|
| Ile | Met | Tyr | Arg | Lys | Phe | Thr | Thr | Glu | Ser | Asp | Val | Trp | Ser | Phe | Gly | |
| | | 730 | | | | | 735 | | | | | 740 | | | | |

| GTG | ATC | CTC | TGG | GAC | ATC | TTC | ACC | TAC | GGA | AAG | CAG | CCA | TGG | TTC | CAA | 2308 |
|---|---|---|---|---|---|---|---|---|---|---|---|---|---|---|---|---|
| Val | Ile | Leu | Trp | Asp | Ile | Phe | Thr | Tyr | Gly | Lys | Gln | Pro | Trp | Phe | Gln | |
| | 745 | | | | | 750 | | | | | 755 | | | | | |

| CTC | TCA | AAC | ACA | GAG | GTC | ATT | GAG | TGC | ATC | ACC | CAA | GGT | CGC | GTT | TTG | 2356 |
|---|---|---|---|---|---|---|---|---|---|---|---|---|---|---|---|---|
| Leu | Ser | Asn | Thr | Glu | Val | Ile | Glu | Cys | Ile | Thr | Gln | Gly | Arg | Val | Leu | |
| 760 | | | | | 765 | | | | | 770 | | | | | 775 | |

| GAA | CGG | CCC | CGG | GTC | TGC | CCC | AAA | GAG | GTG | TAT | GAT | GTC | ATG | CTG | GGG | 2404 |
|---|---|---|---|---|---|---|---|---|---|---|---|---|---|---|---|---|
| Glu | Arg | Pro | Arg | Val | Cys | Pro | Lys | Glu | Val | Tyr | Asp | Val | Met | Leu | Gly | |
| | | | | 780 | | | | | 785 | | | | | 790 | | |

| TGC | TGG | CAG | AGG | GAA | CCG | CAG | CAG | CGG | CTG | AAC | ATC | AAG | GAA | ATC | TAC | 2452 |
|---|---|---|---|---|---|---|---|---|---|---|---|---|---|---|---|---|
| Cys | Trp | Gln | Arg | Glu | Pro | Gln | Gln | Arg | Leu | Asn | Ile | Lys | Glu | Ile | Tyr | |
| | | 795 | | | | | 800 | | | | | 805 | | | | |

| AAA | ATC | CTC | CAT | GCT | TTG | GGG | AAA | GCC | ACC | CCC | ATC | TAC | CTG | GAC | ATC | 2500 |
|---|---|---|---|---|---|---|---|---|---|---|---|---|---|---|---|---|
| Lys | Ile | Leu | His | Ala | Leu | Gly | Lys | Ala | Thr | Pro | Ile | Tyr | Leu | Asp | Ile | |
| | | 810 | | | | | 815 | | | | | 820 | | | | |

| CTT | GGC | TAGCGGTGGC | CGGTGGTCAC | 2526 |
|---|---|---|---|---|
| Leu | Gly | | | |
| | 825 | | | |

( 2 ) INFORMATION FOR SEQ ID NO:2:

( i ) SEQUENCE CHARACTERISTICS:
        ( A ) LENGTH: 825 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Val Ser Leu Cys Pro Ala Lys Ser Ser Phe Trp Arg Ile Phe
 1               5                  10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
            35                  40                  45

Asp Asp Gly Asn Leu Phe Pro Leu Leu Glu Gly Gln Asp Ser Gly Asn
        50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Gly Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
            115                 120                 125

Leu Arg Tyr Ile Asn Leu Ser Ser Asn Arg Leu Thr Thr Leu Ser Trp
        130                 135                 140

Gln Leu Phe Gln Thr Leu Ser Leu Arg Glu Leu Arg Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Ser Leu Tyr Cys Ile Ser Ala
            180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
    210                 215                 220

Asp Asn Ala Val Val Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val His Tyr Pro
    290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Pro Thr Leu His Trp Leu
                325                 330                 335

His Asn Gly Gln Pro Leu Arg Glu Ser Lys Ile Thr His Val Glu Tyr
            340                 345                 350

Tyr Gln Glu Gly Glu Val Ser Glu Gly Cys Leu Leu Phe Asn Lys Pro
        355                 360                 365
```

-continued

| | | | | | | | | | | | | | |
|---|---|---|---|---|---|---|---|---|---|---|---|---|---|
| Thr | His 370 | Tyr | Asn | Asn | Gly 375 | Asn | Tyr | Thr | Leu | Asn 380 | Arg | Gln | Glu | Pro | Leu |
| Gly 385 | Thr | Ala | Asn | Gln | Thr 390 | Ile | Asn | Gly | His | Phe 395 | Leu | Lys | Glu | Pro | Phe 400 |
| Pro | Glu | Ser | Thr | Asp 405 | Asn | Phe | Val | Ser | Phe 410 | Tyr | Glu | Val | Ser 415 | Pro | Thr |
| Pro | Pro | Ile | Thr 420 | Val | Thr | His | Lys | Pro 425 | Glu | Glu | Asp | Thr | Phe 430 | Gly | Val |
| Ser | Ile | Ala 435 | Val | Gly | Leu | Ala | Ala 440 | Phe | Ala | Cys | Val | Leu 445 | Leu | Val | Val |
| Leu | Phe 450 | Ile | Met | Ile | Asn | Lys 455 | Tyr | Gly | Arg | Arg | Ser 460 | Lys | Phe | Gly | Met |
| Lys 465 | Gly | Pro | Val | Ala | Val 470 | Ile | Ser | Gly | Glu | Glu 475 | Asp | Ser | Ala | Ser | Pro 480 |
| Leu | His | His | Asp | Gln 485 | Pro | Trp | His | His | His 490 | Thr | Leu | Ile | Thr | Gly 495 | Arg |
| Arg | Ala | Gly | His | Ser 500 | Val | Ile | Gly | Met | Thr 505 | Arg | Ile | Pro | Val 510 | Ile | Glu |
| Asn | Pro | Gln 515 | Tyr | Phe | Arg | Gln | Gly 520 | His | Asn | Cys | His | Lys 525 | Pro | Asp | Thr |
| Tyr | Val 530 | Gln | His | Ile | Lys | Arg 535 | Arg | Asp | Ile | Val | Leu 540 | Lys | Arg | Glu | Leu |
| Gly 545 | Glu | Gly | Ala | Phe | Gly 550 | Lys | Val | Phe | Leu | Ala 555 | Glu | Cys | Tyr | Asn | Leu 560 |
| Ser | Pro | Thr | Lys | Val 565 | Lys | Met | Leu | Val | Ala 570 | Val | Lys | Ala | Leu | Lys 575 | Asp |
| Pro | Thr | Leu | Ala 580 | Ala | Arg | Lys | Asp | Phe 585 | Gln | Arg | Glu | Ala | Glu 590 | Leu | Leu |
| Thr | Asn | Leu 595 | Gln | His | Glu | His | Ile 600 | Val | Lys | Phe | Tyr | Gly 605 | Val | Cys | Gly |
| Asp | Gly 610 | Asp | Pro | Leu | Ile | Met 615 | Val | Phe | Glu | Tyr | Met 620 | Lys | His | Gly | Asp |
| Leu 625 | Asn | Lys | Phe | Leu | Arg 630 | Ala | Gln | Gly | Pro | Asp 635 | Ala | Met | Ile | Leu | Val 640 |
| Asp | Gly | Gln | Pro | Arg 645 | Gln | Ala | Lys | Gly | Glu 650 | Leu | Gly | Leu | Ser | Gln 655 | Met |
| Leu | His | Ile | Ala 660 | Ser | Gln | Ile | Cys | Ser 665 | Gly | Met | Val | Tyr | Leu 670 | Ala | Ser |
| Gln | His | Phe 675 | Val | His | Arg | Asp | Leu 680 | Ala | Thr | Arg | Asn | Cys 685 | Leu | Val | Gly |
| Ala | Asn 690 | Leu | Leu | Val | Lys | Ile 695 | Gly | Asp | Phe | Gly | Met 700 | Ser | Arg | Asp | Val |
| Tyr 705 | Ser | Thr | Asp | Tyr | Tyr 710 | Arg | Val | Gly | Gly | His 715 | Thr | Met | Leu | Pro | Ile 720 |
| Arg | Trp | Met | Pro | Pro 725 | Glu | Ser | Ile | Met | Tyr 730 | Arg | Lys | Phe | Thr | Thr 735 | Glu |
| Ser | Asp | Val | Trp 740 | Ser | Phe | Gly | Val | Ile 745 | Leu | Trp | Asp | Ile | Phe 750 | Thr | Tyr |
| Gly | Lys | Gln 755 | Pro | Trp | Phe | Gln | Leu 760 | Ser | Asn | Thr | Glu | Val 765 | Ile | Glu | Cys |
| Ile | Thr 770 | Gln | Gly | Arg | Val | Leu 775 | Glu | Arg | Pro | Arg | Val 780 | Cys | Pro | Lys | Glu |
| Val 785 | Tyr | Asp | Val | Met | Leu 790 | Gly | Cys | Trp | Gln | Arg 795 | Glu | Pro | Gln | Gln | Arg 800 |
| Leu | Asn | Ile | Lys | Glu | Ile | Tyr | Lys | Ile | Leu | His | Ala | Leu | Gly | Lys | Ala |

-continued

```
                                805                        810                        815
Thr  Pro  Ile  Tyr  Leu  Asp  Ile  Leu  Gly
                                820                        825
```

( 2 ) INFORMATION FOR SEQ ID NO:3:

( i ) SEQUENCE CHARACTERISTICS:
        ( A ) LENGTH: 2376 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..2184

( i x ) FEATURE:
        ( A ) NAME/KEY: CDS
        ( B ) LOCATION: 32

( x i ) SEQUENCE DESCRIPTION: SEQ ID NO:3:

```
AAT  TCT  GGA  CTC  CGG  AAC  ATC  CAG  CCC  AGA  GCC  TTC  GCC  AAG  AAC  CCC        48
Asn  Ser  Gly  Leu  Arg  Asn  Ile  Gln  Pro  Arg  Ala  Phe  Ala  Lys  Asn  Pro
 1                   5                        10                       15

CAC  TTG  CGT  TAT  ATA  AAC  TTG  TCA  AGT  AAC  CGG  CTC  ACC  ACA  CTC  TCC        96
His  Leu  Arg  Tyr  Ile  Asn  Leu  Ser  Ser  Asn  Arg  Leu  Thr  Thr  Leu  Ser
               20                       25                       30

TGG  CAG  CTC  TTC  CAG  ACG  CTG  AGC  CTT  CGG  GAA  TTG  AGA  CTG  GAG  CAG       144
Trp  Gln  Leu  Phe  Gln  Thr  Leu  Ser  Leu  Arg  Glu  Leu  Arg  Leu  Glu  Gln
          35                       40                       45

AAC  TTC  TTC  AAC  TGC  AGC  TGT  GAC  ATC  CGC  TGG  ATG  CAG  CTG  TGG  CAG       192
Asn  Phe  Phe  Asn  Cys  Ser  Cys  Asp  Ile  Arg  Trp  Met  Gln  Leu  Trp  Gln
     50                       55                       60

GAA  CAG  GGG  GAG  GCG  CGG  CTG  GAC  AGC  CAG  AGC  CTT  TAC  TGC  ATC  AGT       240
Glu  Gln  Gly  Glu  Ala  Arg  Leu  Asp  Ser  Gln  Ser  Leu  Tyr  Cys  Ile  Ser
65                        70                       75                       80

GCT  GAT  GGC  TCC  CAA  CTC  CCC  CTC  TTC  CGC  ATG  AAC  ATC  AGT  CAG  TGT       288
Ala  Asp  Gly  Ser  Gln  Leu  Pro  Leu  Phe  Arg  Met  Asn  Ile  Ser  Gln  Cys
                    85                       90                       95

GAT  CTC  CCA  GAG  ATC  AGT  GTG  AGC  CAC  GTC  AAC  CTG  ACT  GTC  CGA  GAA       336
Asp  Leu  Pro  Glu  Ile  Ser  Val  Ser  His  Val  Asn  Leu  Thr  Val  Arg  Glu
               100                      105                      110

GGA  GAC  AAT  GCC  GTG  ATC  ACT  TGC  AAT  GGC  TCT  GGC  TCT  CCT  TTG  CCT       384
Gly  Asp  Asn  Ala  Val  Ile  Thr  Cys  Asn  Gly  Ser  Gly  Ser  Pro  Leu  Pro
          115                      120                      125

GAT  GTG  GAC  TGG  ATA  GTC  ACT  GGG  CTG  CAG  TCC  ATC  AAC  ACC  CAC  CAG       432
Asp  Val  Asp  Trp  Ile  Val  Thr  Gly  Leu  Gln  Ser  Ile  Asn  Thr  His  Gln
    130                      135                      140

ACC  AAT  CTG  AAC  TGG  ACC  AAT  GTA  CAT  GCC  ATC  AAC  TTG  ACC  CTG  GTG       480
Thr  Asn  Leu  Asn  Trp  Thr  Asn  Val  His  Ala  Ile  Asn  Leu  Thr  Leu  Val
145                      150                      155                      160

AAC  GTG  ACG  AGC  GAG  GAC  AAT  GGC  TTC  ACC  CTG  ACG  TGC  ATT  GCA  GAG       528
Asn  Val  Thr  Ser  Glu  Asp  Asn  Gly  Phe  Thr  Leu  Thr  Cys  Ile  Ala  Glu
                    165                      170                      175

AAC  GTG  GTG  GGC  ATG  AGC  AAT  GCC  AGT  GTT  GCT  CTC  ACT  GTC  TAC  TAC       576
Asn  Val  Val  Gly  Met  Ser  Asn  Ala  Ser  Val  Ala  Leu  Thr  Val  Tyr  Tyr
               180                      185                      190

CCT  CCA  CGT  GTG  GTG  AGC  CTG  GTG  GAG  CCT  GAG  GTA  CGC  CTG  GAA  CAT       624
Pro  Pro  Arg  Val  Val  Ser  Leu  Val  Glu  Pro  Glu  Val  Arg  Leu  Glu  His
          195                      200                      205

TGC  ATT  GAG  TTT  GTG  GTG  CGT  GGC  AAC  CCG  ACA  CCC  ACG  CTC  CAC  TGG       672
Cys  Ile  Glu  Phe  Val  Val  Arg  Gly  Asn  Pro  Thr  Pro  Thr  Leu  His  Trp
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 210 |     |     |     |     | 215 |     |     |     |     |     | 220 |     |     |     |      |
| CTG | TAC | AAT | GGA | CAG | CCA | TTG | AGG | GAG | TCC | AAG | ATC | ATT | CAC | ATG | GAC | 720  |
| Leu | Tyr | Asn | Gly | Gln | Pro | Leu | Arg | Glu | Ser | Lys | Ile | Ile | His | Met | Asp |      |
| 225 |     |     |     | 230 |     |     |     |     | 235 |     |     |     |     | 240 |     |      |
| TAC | TAC | CAG | GAG | GGG | GAG | GTC | TCA | GAG | GGC | TGC | CTG | CTC | TTC | AAC | AAG | 768  |
| Tyr | Tyr | Gln | Glu | Gly | Glu | Val | Ser | Glu | Gly | Cys | Leu | Leu | Phe | Asn | Lys |      |
|     |     |     |     | 245 |     |     |     |     | 250 |     |     |     |     | 255 |     |      |
| CCC | ACC | CAC | TAC | AAC | AAT | GGC | AAC | TAC | ACC | CTC | ATT | GCT | AAG | AAT | GCC | 816  |
| Pro | Thr | His | Tyr | Asn | Asn | Gly | Asn | Tyr | Thr | Leu | Ile | Ala | Lys | Asn | Ala |      |
|     |     | 260 |     |     |     |     | 265 |     |     |     |     |     | 270 |     |     |      |
| CTG | GGC | ACG | GCC | AAC | CAG | ACC | ATC | AAC | GGC | CAC | TTC | CTG | AAG | GAG | CCC | 864  |
| Leu | Gly | Thr | Ala | Asn | Gln | Thr | Ile | Asn | Gly | His | Phe | Leu | Lys | Glu | Pro |      |
|     |     | 275 |     |     |     |     | 280 |     |     |     |     | 285 |     |     |     |      |
| TTT | CCA | GAG | AGC | ACA | GAT | TTC | TTT | GAC | TTT | GAG | TCT | GAT | GCG | AGC | CCT | 912  |
| Phe | Pro | Glu | Ser | Thr | Asp | Phe | Phe | Asp | Phe | Glu | Ser | Asp | Ala | Ser | Pro |      |
|     | 290 |     |     |     |     | 295 |     |     |     |     | 300 |     |     |     |     |      |
| ACA | CCT | CCT | ATC | ACT | GTG | ACC | CAC | AAA | CCA | GAG | GAA | GAC | ACT | TTT | GGG | 960  |
| Thr | Pro | Pro | Ile | Thr | Val | Thr | His | Lys | Pro | Glu | Glu | Asp | Thr | Phe | Gly |      |
| 305 |     |     |     |     | 310 |     |     |     |     | 315 |     |     |     |     | 320 |      |
| GTG | TCC | ATA | GCA | GTC | GGA | CTT | GCT | GCC | TTT | GCC | TGC | GTC | CTT | CTG | GTG | 1008 |
| Val | Ser | Ile | Ala | Val | Gly | Leu | Ala | Ala | Phe | Ala | Cys | Val | Leu | Leu | Val |      |
|     |     |     |     | 325 |     |     |     |     | 330 |     |     |     |     | 335 |     |      |
| GTT | CTC | TTT | ATC | ATG | ATC | AAC | AAG | TAT | GGT | CGC | CGG | TCC | AAA | TTT | GGA | 1056 |
| Val | Leu | Phe | Ile | Met | Ile | Asn | Lys | Tyr | Gly | Arg | Arg | Ser | Lys | Phe | Gly |      |
|     |     |     | 340 |     |     |     |     | 345 |     |     |     |     | 350 |     |     |      |
| ATG | AAG | GGT | CCT | GTG | GCT | GTT | ATC | AGT | GGA | GAG | GAG | GAC | TCA | GCC | AGC | 1104 |
| Met | Lys | Gly | Pro | Val | Ala | Val | Ile | Ser | Gly | Glu | Glu | Asp | Ser | Ala | Ser |      |
|     |     | 355 |     |     |     |     | 360 |     |     |     |     | 365 |     |     |     |      |
| CCA | CTG | CAT | CAC | GAT | CAA | CCA | TGG | CAT | CAC | TAC | ACC | ATC | ATC | GTT | GGA | 1152 |
| Pro | Leu | His | His | Asp | Gln | Pro | Trp | His | His | Tyr | Thr | Ile | Ile | Val | Gly |      |
|     | 370 |     |     |     |     | 375 |     |     |     |     | 380 |     |     |     |     |      |
| TGC | TGG | GCC | GTA | CAC | GTG | GTC | ATT | GGC | ATG | ACC | CGC | ATC | CCA | GTC | ATT | 1200 |
| Cys | Trp | Ala | Val | His | Val | Val | Ile | Gly | Met | Thr | Arg | Ile | Pro | Val | Ile |      |
| 385 |     |     |     |     | 390 |     |     |     |     | 395 |     |     |     |     | 400 |      |
| GAG | AAC | CCC | CAG | TAC | TTC | CGT | CAG | GGT | CAC | AAT | TGC | CAC | AAG | CCA | GAC | 1248 |
| Glu | Asn | Pro | Gln | Tyr | Phe | Arg | Gln | Gly | His | Asn | Cys | His | Lys | Pro | Asp |      |
|     |     |     |     | 405 |     |     |     |     | 410 |     |     |     |     | 415 |     |      |
| ACA | TAT | GTT | CAG | CAC | ATC | AAG | AGG | AGA | GAC | ATC | GTG | TTG | AAG | AGA | GAA | 1296 |
| Thr | Tyr | Val | Gln | His | Ile | Lys | Arg | Arg | Asp | Ile | Val | Leu | Lys | Arg | Glu |      |
|     |     |     | 420 |     |     |     |     | 425 |     |     |     |     | 430 |     |     |      |
| TTG | GGT | GAG | GGA | GCC | TTT | GGG | AAG | GTC | TTC | CTG | GCT | GAG | TGC | TAC | AAT | 1344 |
| Leu | Gly | Glu | Gly | Ala | Phe | Gly | Lys | Val | Phe | Leu | Ala | Glu | Cys | Tyr | Asn |      |
|     |     | 435 |     |     |     |     | 440 |     |     |     |     | 445 |     |     |     |      |
| CTA | AGC | CCC | ACC | AAA | GAC | AAG | ATG | CTA | GTG | GCA | GTG | AAG | GCC | CTG | AAG | 1392 |
| Leu | Ser | Pro | Thr | Lys | Asp | Lys | Met | Leu | Val | Ala | Val | Lys | Ala | Leu | Lys |      |
|     | 450 |     |     |     |     | 455 |     |     |     |     | 460 |     |     |     |     |      |
| GAT | CCC | ACC | TTG | GCT | GCC | AGG | AAG | GAT | TTC | CAG | AGG | GAG | GCT | GAG | CTG | 1440 |
| Asp | Pro | Thr | Leu | Ala | Ala | Arg | Lys | Asp | Phe | Gln | Arg | Glu | Ala | Glu | Leu |      |
| 465 |     |     |     |     | 470 |     |     |     |     | 475 |     |     |     |     | 480 |      |
| CTC | ACG | AAC | CTG | CAG | CAT | GAG | CAT | ATT | GTC | AAG | TTC | TAT | GGG | GTG | TGT | 1488 |
| Leu | Thr | Asn | Leu | Gln | His | Glu | His | Ile | Val | Lys | Phe | Tyr | Gly | Val | Cys |      |
|     |     |     |     | 485 |     |     |     |     | 490 |     |     |     |     | 495 |     |      |
| GGT | GAT | GGT | GAC | CCA | CTC | ATC | ATG | GTC | TTT | GAA | TAC | ATG | AAG | CAT | GGA | 1536 |
| Gly | Asp | Gly | Asp | Pro | Leu | Ile | Met | Val | Phe | Glu | Tyr | Met | Lys | His | Gly |      |
|     |     |     | 500 |     |     |     |     | 505 |     |     |     |     | 510 |     |     |      |
| GAC | CTT | AAC | AAG | TTC | CTC | AGG | GCC | CAT | GGG | CCA | GAT | GCC | ATG | ATC | CTC | 1584 |
| Asp | Leu | Asn | Lys | Phe | Leu | Arg | Ala | His | Gly | Pro | Asp | Ala | Met | Ile | Leu |      |
|     |     | 515 |     |     |     |     | 520 |     |     |     |     | 525 |     |     |     |      |
| GTG | GAT | GGA | CAG | CCA | CGT | CAG | GCC | AAG | GGG | GAG | CTA | GGG | CTC | TCT | CAG | 1632 |
| Val | Asp | Gly | Gln | Pro | Arg | Gln | Ala | Lys | Gly | Glu | Leu | Gly | Leu | Ser | Gln |      |
|     | 530 |     |     |     |     | 535 |     |     |     |     | 540 |     |     |     |     |      |

| | | | | | | | | | | | | | | | | |
|---|---|---|---|---|---|---|---|---|---|---|---|---|---|---|---|---|
| ATG | CTC | CAC | ATC | GCC | AGT | CAG | ATA | GCC | TCG | GGC | ATG | GTG | TAC | CTG | GCT | 1680 |
| Met | Leu | His | Ile | Ala | Ser | Gln | Ile | Ala | Ser | Gly | Met | Val | Tyr | Leu | Ala | |
| 545 | | | | 550 | | | | | 555 | | | | | 560 | | |
| TCC | CAG | CAC | TTT | GTA | CAC | CGG | GAC | CTG | GCC | ACG | AGG | AAC | TGC | CTG | GTT | 1728 |
| Ser | Gln | His | Phe | Val | His | Arg | Asp | Leu | Ala | Thr | Arg | Asn | Cys | Leu | Val | |
| | | | | 565 | | | | 570 | | | | | 575 | | | |
| GGA | GCC | AAT | CTA | CTA | GTG | AAG | ATT | GGA | GAT | TTT | GGC | ATG | TCC | AGG | GAC | 1776 |
| Gly | Ala | Asn | Leu | Leu | Val | Lys | Ile | Gly | Asp | Phe | Gly | Met | Ser | Arg | Asp | |
| | | | 580 | | | | | 585 | | | | | 590 | | | |
| GTC | TAC | AGT | ACT | GAT | TAC | TAC | AGG | CTC | TTT | AAT | CCA | TCT | GGA | AAT | GAT | 1824 |
| Val | Tyr | Ser | Thr | Asp | Tyr | Tyr | Arg | Leu | Phe | Asn | Pro | Ser | Gly | Asn | Asp | |
| | | 595 | | | | | 600 | | | | | 605 | | | | |
| TTT | TGT | ATA | TGG | TGT | GAG | GTG | GGA | GGA | CAC | ACC | ATG | CTC | CCC | ATC | CGC | 1872 |
| Phe | Cys | Ile | Trp | Cys | Glu | Val | Gly | Gly | His | Thr | Met | Leu | Pro | Ile | Arg | |
| 610 | | | | | 615 | | | | | 620 | | | | | | |
| TGG | ATG | CCC | CCT | GAA | AGC | ATA | ATG | TAC | CGG | AAG | TTC | ACC | ACA | GAG | AGT | 1920 |
| Trp | Met | Pro | Pro | Glu | Ser | Ile | Met | Tyr | Arg | Lys | Phe | Thr | Thr | Glu | Ser | |
| 625 | | | | | 630 | | | | | 635 | | | | | 640 | |
| GAT | GTC | TGG | AGC | TTC | GGG | GTT | ATT | CTT | TGG | GAG | ATC | TTT | ACC | TAT | GGG | 1968 |
| Asp | Val | Trp | Ser | Phe | Gly | Val | Ile | Leu | Trp | Glu | Ile | Phe | Thr | Tyr | Gly | |
| | | | | 645 | | | | | 650 | | | | | 655 | | |
| AAG | CAA | CCA | TGG | TTC | CAG | CTT | TCC | AAC | ACG | GAG | GTC | ATT | GAA | TGC | ATC | 2016 |
| Lys | Gln | Pro | Trp | Phe | Gln | Leu | Ser | Asn | Thr | Glu | Val | Ile | Glu | Cys | Ile | |
| | | | 660 | | | | | 665 | | | | | 670 | | | |
| ACC | CAA | GGC | CGT | GTC | TTG | GAG | AGA | CCC | AGA | GTC | TGC | CCT | AAA | GAA | GTG | 2064 |
| Thr | Gln | Gly | Arg | Val | Leu | Glu | Arg | Pro | Arg | Val | Cys | Pro | Lys | Glu | Val | |
| | | 675 | | | | | 680 | | | | | 685 | | | | |
| TAT | GAT | GTC | ATG | CTG | GGG | TGC | TGG | CAG | AGG | GAA | CCA | CAG | CAG | CGG | CTG | 2112 |
| Tyr | Asp | Val | Met | Leu | Gly | Cys | Trp | Gln | Arg | Glu | Pro | Gln | Gln | Arg | Leu | |
| | 690 | | | | | 695 | | | | | 700 | | | | | |
| AAT | ATT | AAG | GAG | ATC | TAC | AAA | ATC | CTC | CAT | GCT | TTG | GGG | AAG | GCC | ACC | 2160 |
| Asn | Ile | Lys | Glu | Ile | Tyr | Lys | Ile | Leu | His | Ala | Leu | Gly | Lys | Ala | Thr | |
| 705 | | | | | 710 | | | | | 715 | | | | | 720 | |
| CCG | ATC | TAC | CTG | GAC | ATT | CTT | GGC | TAGTGGTGAC | | TGGTGGCCAA | | GCATTTATAC | | | | 2214 |
| Pro | Ile | Tyr | Leu | Asp | Ile | Leu | Gly | | | | | | | | | |
| | | | | 725 | | | | | | | | | | | | |

| | | | | |
|---|---|---|---|---|
| TCTGTTGCCT | CCTCTCTCCC | TGCTTCCTTT | CCTCTTTTTC | CTCATCTCAA | CTCCTTTCTT | 2274 |
| CCATTTTTGA | CGGAAACGAA | CATCTTCATA | TAAACTCAAG | TGCCTGCTAC | ACATACAACA | 2334 |
| CTGAATTTAA | ACAAAACAAA | ACAAAAAAAA | AAAGGAATT | CC | | 2376 |

( 2 ) INFORMATION FOR SEQ ID NO:4:

( i ) SEQUENCE CHARACTERISTICS:
        ( A ) LENGTH: 728 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Asn | Ser | Gly | Leu | Arg | Asn | Ile | Gln | Pro | Arg | Ala | Phe | Ala | Lys | Asn | Pro |
| 1 | | | | 5 | | | | | 10 | | | | | 15 | |
| His | Leu | Arg | Tyr | Ile | Asn | Leu | Ser | Ser | Asn | Arg | Leu | Thr | Thr | Leu | Ser |
| | | | 20 | | | | | 25 | | | | | 30 | | |
| Trp | Gln | Leu | Phe | Gln | Thr | Leu | Ser | Leu | Arg | Glu | Leu | Arg | Leu | Glu | Gln |
| | | 35 | | | | | 40 | | | | | 45 | | | |
| Asn | Phe | Phe | Asn | Cys | Ser | Cys | Asp | Ile | Arg | Trp | Met | Gln | Leu | Trp | Gln |
| | 50 | | | | | 55 | | | | | 60 | | | | |
| Glu | Gln | Gly | Glu | Ala | Arg | Leu | Asp | Ser | Gln | Ser | Leu | Tyr | Cys | Ile | Ser |
| 65 | | | | | 70 | | | | | 75 | | | | | 80 |
| Ala | Asp | Gly | Ser | Gln | Leu | Pro | Leu | Phe | Arg | Met | Asn | Ile | Ser | Gln | Cys |

-continued

|  |  |  | 85 |  |  |  | 90 |  |  |  | 95 |  |  |
|---|---|---|---|---|---|---|---|---|---|---|---|---|---|

Asp Leu Pro Glu Ile Ser Val Ser His Val Asn Leu Thr Val Arg Glu
                100                 105                110

Gly Asp Asn Ala Val Ile Thr Cys Asn Gly Ser Gly Ser Pro Leu Pro
            115                 120                 125

Asp Val Asp Trp Ile Val Thr Gly Leu Gln Ser Ile Asn Thr His Gln
        130                 135                 140

Thr Asn Leu Asn Trp Thr Asn Val His Ala Ile Asn Leu Thr Leu Val
145                 150                 155                 160

Asn Val Thr Ser Glu Asp Asn Gly Phe Thr Leu Thr Cys Ile Ala Glu
                165                 170                 175

Asn Val Val Gly Met Ser Asn Ala Ser Val Ala Leu Thr Val Tyr Tyr
            180                 185                 190

Pro Pro Arg Val Val Ser Leu Val Glu Pro Glu Val Arg Leu Glu His
        195                 200                 205

Cys Ile Glu Phe Val Val Arg Gly Asn Pro Thr Pro Thr Leu His Trp
210                 215                 220

Leu Tyr Asn Gly Gln Pro Leu Arg Glu Ser Lys Ile Ile His Met Asp
225                 230                 235                 240

Tyr Tyr Gln Glu Gly Glu Val Ser Glu Gly Cys Leu Leu Phe Asn Lys
                245                 250                 255

Pro Thr His Tyr Asn Asn Gly Asn Tyr Thr Leu Ile Ala Lys Asn Ala
            260                 265                 270

Leu Gly Thr Ala Asn Gln Thr Ile Asn Gly His Phe Leu Lys Glu Pro
        275                 280                 285

Phe Pro Glu Ser Thr Asp Phe Phe Asp Phe Glu Ser Asp Ala Ser Pro
290                 295                 300

Thr Pro Pro Ile Thr Val Thr His Lys Pro Glu Glu Asp Thr Phe Gly
305                 310                 315                 320

Val Ser Ile Ala Val Gly Leu Ala Ala Phe Ala Cys Val Leu Leu Val
                325                 330                 335

Val Leu Phe Ile Met Ile Asn Lys Tyr Gly Arg Arg Ser Lys Phe Gly
            340                 345                 350

Met Lys Gly Pro Val Ala Val Ile Ser Gly Glu Glu Asp Ser Ala Ser
        355                 360                 365

Pro Leu His His Asp Gln Pro Trp His His Tyr Thr Ile Ile Val Gly
370                 375                 380

Cys Trp Ala Val His Val Val Ile Gly Met Thr Arg Ile Pro Val Ile
385                 390                 395                 400

Glu Asn Pro Gln Tyr Phe Arg Gln Gly His Asn Cys His Lys Pro Asp
                405                 410                 415

Thr Tyr Val Gln His Ile Lys Arg Arg Asp Ile Val Leu Lys Arg Glu
            420                 425                 430

Leu Gly Glu Gly Ala Phe Gly Lys Val Phe Leu Ala Glu Cys Tyr Asn
        435                 440                 445

Leu Ser Pro Thr Lys Asp Lys Met Leu Val Ala Val Lys Ala Leu Lys
450                 455                 460

Asp Pro Thr Leu Ala Ala Arg Lys Asp Phe Gln Arg Glu Ala Glu Leu
465                 470                 475                 480

Leu Thr Asn Leu Gln His Glu His Ile Val Lys Phe Tyr Gly Val Cys
                485                 490                 495

Gly Asp Gly Asp Pro Leu Ile Met Val Phe Glu Tyr Met Lys His Gly
            500                 505                 510

Asp Leu Asn Lys Phe Leu Arg Ala His Gly Pro Asp Ala Met Ile Leu
        515                 520                 525

| | | | | | | | | | | | | | | |
|---|---|---|---|---|---|---|---|---|---|---|---|---|---|---|
|Val|Asp|Gly|Gln|Pro|Arg|Gln|Ala|Lys|Gly|Glu|Leu|Gly|Leu|Ser|Gln|
| |530| | | |535| | | |540| | | | | |
|Met|Leu|His|Ile|Ala|Ser|Gln|Ile|Ala|Ser|Gly|Met|Val|Tyr|Leu|Ala|
|545| | | | |550| | | |555| | | | | |560|
|Ser|Gln|His|Phe|Val|His|Arg|Asp|Leu|Ala|Thr|Arg|Asn|Cys|Leu|Val|
| | | | |565| | | | |570| | | | |575| |
|Gly|Ala|Asn|Leu|Leu|Val|Lys|Ile|Gly|Asp|Phe|Gly|Met|Ser|Arg|Asp|
| | | |580| | | | |585| | | | |590| | |
|Val|Tyr|Ser|Thr|Asp|Tyr|Tyr|Arg|Leu|Phe|Asn|Pro|Ser|Gly|Asn|Asp|
| | |595| | | | |600| | | | |605| | | |
|Phe|Cys|Ile|Trp|Cys|Glu|Val|Gly|Gly|His|Thr|Met|Leu|Pro|Ile|Arg|
| |610| | | | |615| | | | |620| | | | |
|Trp|Met|Pro|Pro|Glu|Ser|Ile|Met|Tyr|Arg|Lys|Phe|Thr|Thr|Glu|Ser|
|625| | | | |630| | | | |635| | | | |640|
|Asp|Val|Trp|Ser|Phe|Gly|Val|Ile|Leu|Trp|Glu|Ile|Phe|Thr|Tyr|Gly|
| | | | |645| | | | |650| | | | |655| |
|Lys|Gln|Pro|Trp|Phe|Gln|Leu|Ser|Asn|Thr|Glu|Val|Ile|Glu|Cys|Ile|
| | | |660| | | | |665| | | | |670| | |
|Thr|Gln|Gly|Arg|Val|Leu|Glu|Arg|Pro|Arg|Val|Cys|Pro|Lys|Glu|Val|
| | |675| | | | |680| | | | |685| | | |
|Tyr|Asp|Val|Met|Leu|Gly|Cys|Trp|Gln|Arg|Glu|Pro|Gln|Gln|Arg|Leu|
| |690| | | | |695| | | | |700| | | | |
|Asn|Ile|Lys|Glu|Ile|Tyr|Lys|Ile|Leu|His|Ala|Leu|Gly|Lys|Ala|Thr|
|705| | | | |710| | | | |715| | | | |720|
|Pro|Ile|Tyr|Leu|Asp|Ile|Leu|Gly| | | | | | | | |
| | | | |725| | | | | | | | | | | |

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CACGAGGAAT TCCCTGGTTG GAGCCAATCT ACTAGTG 37

( 2 ) INFORMATION FOR SEQ ID NO:6:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CGAAGCTCTA GACATCACTC TCTGTGGTGA ACTTCCGGTA C 41

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTCTTTAATC CATCTGGAAA TGATTTTTGT ATATGCTGTG AG    42

( 2 ) INFORMATION FOR SEQ ID NO:8:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GAAGGGCCAT GCCAGAAGGG CCCATTCAAC GTGTCGTGGC AGCAGCAGAG GCTAGCAGCG    60

TCAGCAGCTT CCACA    75

( 2 ) INFORMATION FOR SEQ ID NO:9:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ATCAACCATG GCATCACCAC ACCCTCATCA GTGGACGCCG GGCCGGACAC AGTGTCATTG    60

GCATGA    66

( 2 ) INFORMATION FOR SEQ ID NO:10:

( i ) SEQUENCE CHARACTERISTICS:
        ( A ) LENGTH: 111 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AAGGTGTTGT TTTTTCAGTC CCAAGAGTTC CATGGTTTCC ACCTATTGAT CAAAAGATAC    60

TGTACCTCCA TATGCTCTCT GCGAAAGCCT TTGGTCACTG GACCTTGGTA A    111